(12) United States Patent  
Sato et al.

(10) Patent No.: US 8,740,791 B2  
(45) Date of Patent: Jun. 3, 2014

(54) BIOLOGICAL INFORMATION DETECTOR AND BIOLOGICAL INFORMATION MEASUREMENT DEVICE

(75) Inventors: Shigemi Sato, Nagano (JP); Yoshitaka Iijima, Nagano (JP); Hideto Yamashita, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 704 days.

(21) Appl. No.: 12/973,313

(22) Filed: Dec. 20, 2010

(65) Prior Publication Data

US 2011/0166457 A1 Jul. 7, 2011

(30) Foreign Application Priority Data

Jan. 5, 2010 (JP) ................................ 2010-000451

(51) Int. Cl.
*A61B 5/00* (2006.01)

(52) U.S. Cl.
USPC ............ 600/300; 324/476; 324/479; 324/502

(58) Field of Classification Search
USPC .......................... 600/324, 344, 500, 502, 503
See application file for complete search history.

(56) References Cited

U.S. PATENT DOCUMENTS

| | | | | |
|---|---|---|---|---|
| 4,685,464 | A | * | 8/1987 | Goldberger et al. .......... 600/344 |
| 4,880,304 | A | | 11/1989 | Jaeb et al. |
| 5,237,994 | A | | 8/1993 | Goldberger |
| 5,553,616 | A | | 9/1996 | Ham et al. |
| 5,995,856 | A | | 11/1999 | Mannheimer et al. |
| 6,041,247 | A | | 3/2000 | Weckstrom et al. |
| 6,134,459 | A | * | 10/2000 | Roberts et al. ................ 600/333 |
| 2002/0188210 | A1 | * | 12/2002 | Aizawa .......................... 600/503 |
| 2005/0253047 | A1 | | 11/2005 | Maegawa et al. |
| 2005/0267346 | A1 | | 12/2005 | Faber et al. |
| 2008/0108885 | A1 | * | 5/2008 | Colvin, Jr. .................... 600/317 |
| 2009/0156918 | A1 | * | 6/2009 | Davis et al. .................. 600/342 |
| 2009/0163775 | A1 | | 6/2009 | Barrett et al. |
| 2009/0299675 | A1 | | 12/2009 | Isaacson et al. |

FOREIGN PATENT DOCUMENTS

| | | |
|---|---|---|
| EP | 1297784 A1 | 4/2003 |
| EP | 1444948 A1 | 8/2004 |
| JP | 2004-337605 A | 12/2004 |
| WO | WO-99/12469 A1 | 3/1999 |
| WO | WO-01/80934 A1 | 11/2001 |
| WO | WO-2009/033189 A1 | 3/2009 |

OTHER PUBLICATIONS

Extended European Search Report dated Apr. 28, 2011 for the counterpart European Application No. 10197367.5.

* cited by examiner

*Primary Examiner* — Navin Natnithithadha
*Assistant Examiner* — Etsub Berhanu
(74) *Attorney, Agent, or Firm* — Global IP Counselors, LLP

(57) ABSTRACT

A biological information detector includes a first sensor unit for detecting composite information including biological information of a test subject and first noise information originating in external light, having a first light-emitting part for emitting toward there, a first light-receiving part for receiving it including the biological information, reflected there, and the light including the first noise information obtained from the external light, transmitted through there, and a first reflecting and leading part for reflecting the light including the biological and the first noise information, leading it to the first light-receiving part, and a second sensor unit for detecting second noise information originating in the external light, having a second light-receiving part for receiving the light including the second noise information, obtained from the external light and transmitted through there, and a second reflecting, leading part for reflecting the external light and leading it to the second light-receiving part.

15 Claims, 18 Drawing Sheets

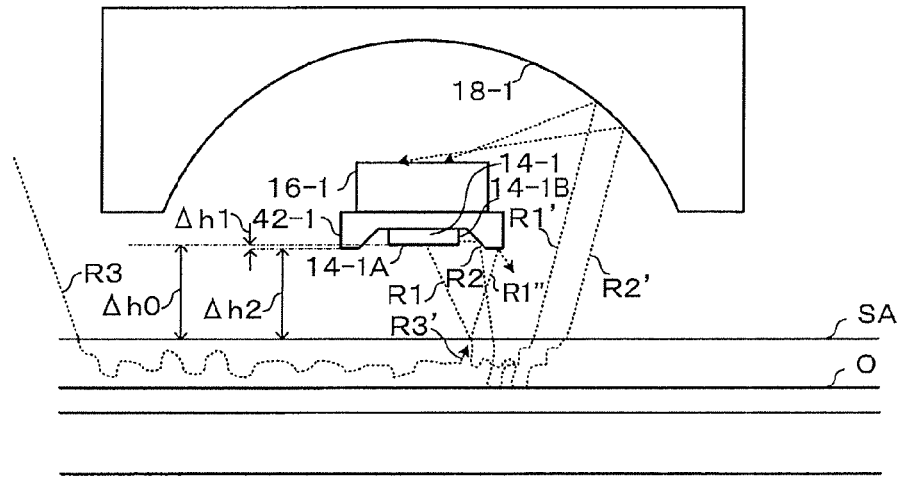
Fig. 4
(A)
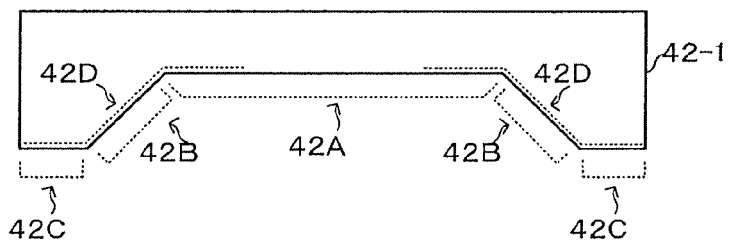
(B)
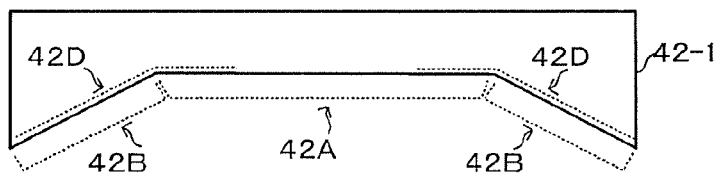
(C)
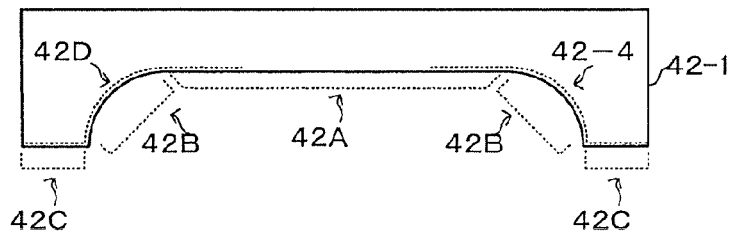
Fig. 5

(A)
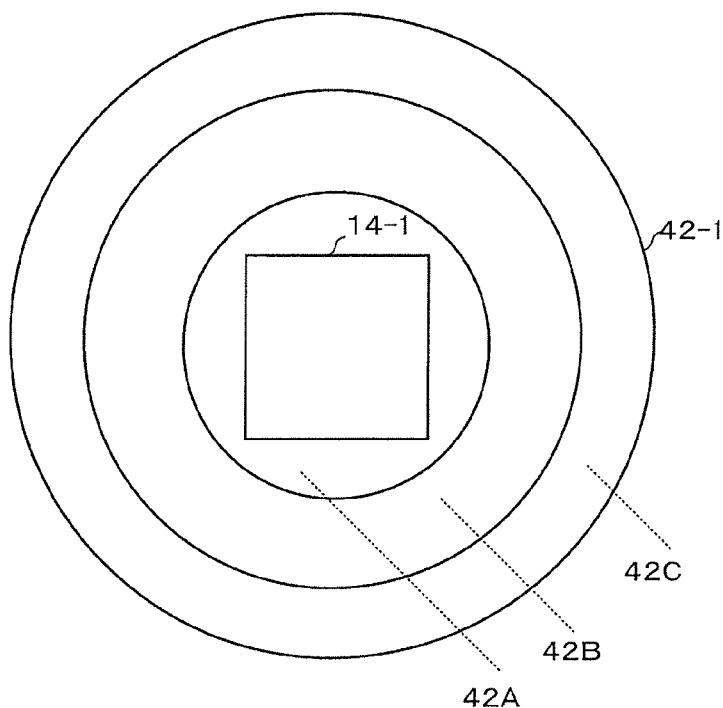
(B)
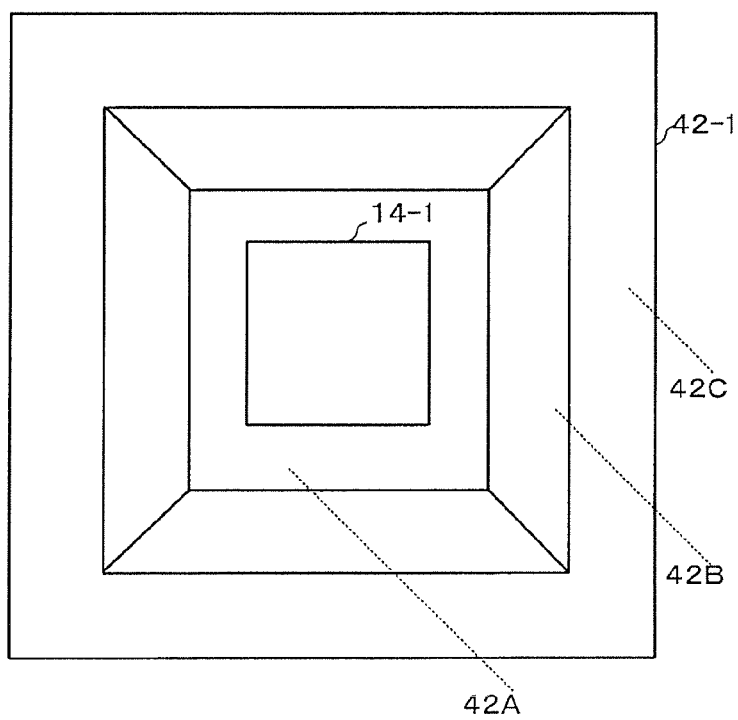
Fig. 6

BIOLOGICAL INFORMATION DETECTOR AND BIOLOGICAL INFORMATION MEASUREMENT DEVICE

BACKGROUND

1. Technological Field

The present invention relates to a biological information detector, a biological information measurement device, and the like.

2. Background Technology

A biological information measurement device is used for measuring, for example, human pulse count, oxygen concentration in the blood, body temperature, heart rate, or other biological information; an example of which biological information measurement device including a pulsometer for measuring pulse count. A pulsometer or other biological information measurement device also may be incorporated in, or combined with, a timepiece, portable telephone, pager, PC, or other electronic device. A biological information measurement device has a biological information detector for detecting biological information, and the biological information detector includes a light-emitting part for emitting light toward a detection site of a test subject (user), and a light-receiving part for receiving light including the biological information from the detection site.

Patent Citation 1 discloses a pulsometer (in the broad sense, a biological information measurement device). Each of a first light-receiving part and a second light-receiving part (e.g., photodiodes 32 and 33 in FIG. 4 of Patent Citation 1) of the pulse measurement device is used for detecting a noise component (e.g., electrical current ic in FIG. 5 of Patent Citation 1) originating in external light. In the pulse measurement device 1 of Patent Citation 1, the electrical current ic of the photodiode 32 and the electrical current of the photodiode 33 are cancelled out. In other words, in the pulse measurement device 1 of Patent Citation 1, the noise component originating in external light is removed, and the accuracy of detecting of biological information is improved.

PRIOR ART REFERENCE

Patent Citation

Patent Citation 1: International Patent Publication No. 99/12469 is an example of related art.

SUMMARY

Technical Problem

Patent Citation 1 discloses that the noise component originating in external light is removed by providing a first light-receiving part and a second light-receiving part. However, the noise component received by the first light-receiving part and the noise component received by the second light-receiving part may not necessarily be equal depending on the arrangement, size, and shape of the first light-receiving part and the second light-receiving part. If the noise component received by the first light-receiving part and the noise component received by the second light-receiving part are not equal, the noise component originating in the external light cannot be suitably removed, and there is a problem that the detecting accuracy or measurement accuracy cannot be improved.

According to a number of modes of the present invention, a biological information detector and a biological information measurement device in which the detecting accuracy or measurement accuracy can be improved can be provided.

Technical Solution

A first aspect of the present invention relates to a biological information detector, characterized in comprising: a first sensor unit for detecting composite information including biological information of a detection site of a test subject and first noise information originating in external light; and a second sensor unit for detecting second noise information originating in the external light; the first sensor unit having: a light-emitting part for emitting a first light toward the detection site; a first light-receiving part for receiving the light including the biological information obtained from the first light emitted toward the detection site being reflected by the detection site, and the light including the first noise information obtained from the external light being transmitted through the test subject; and a first reflecting part for reflecting the light including the biological information and the light including the first noise information and leading the light to the first light-receiving part; and the second sensor unit having: a second light-receiving part for receiving the light including the second noise information obtained from the external light being transmitted through the test subject; and a second reflecting part for reflecting the light including the second noise information and leading the light to the second light-receiving part.

According to the first aspect of the present invention, the light emitted by the light-emitting part is reflected by the detection site, and is then reflected also by the first reflecting part. In other words, the light reflected by the detection site reaches the first light-receiving part by way of the first reflecting part, but is suppressed from reaching the second light-receiving part. Accordingly, the first light-receiving part efficiently receives the light emitted by a first light-emitting part, but the second light-receiving part receives almost no light emitted by the first light-emitting part. The second light-receiving part thus is independent from the first light-receiving part, and can efficiently sense the second noise information originating in the external light transmitted through the test subject. Here, the light including the first noise information obtained from the external light being transmitted through the test subject also is received by the first light-receiving part, but the biological information in the detection site can be efficiently detected upon correction or cancellation of the first noise information by the second noise information. The detecting accuracy (S/N ratio) of the biological information detector is thereby improved.

According to a second aspect of the present invention, a relation S2<S1 may be satisfied, where S1 is an area of a reflecting surface of the first reflecting part, and S2 is an area of a reflecting surface of the second reflecting part.

Because the first sensor unit has a light-emitting part, a part of the external light transmitted through the test subject is blocked or reflected by the light-emitting part, and is suppressed from reaching the first reflecting part. That is, the amount of external light reaching the first reflecting part is made less than the amount of external light reaching the second reflecting part, by the amount blocked or reflected by the light-emitting part. Therefore, by satisfying the relation S2<S1, the amount of external light transmitted through the test subject is suppressed from reaching the second reflecting part, by the amount of reduction of area (S1−S2) of the reflecting surface of the second reflecting part. The difference between the amount of external light received by the second light-receiving part and the amount of external light received by the first light-receiving part can thus be reduced. The first noise information detected by the first sensor unit and the second noise information detected by the second sensor unit can thereby be more accurately corrected or cancelled, and the detecting accuracy of the biological information detector is further improved.

According to a third aspect of the present invention: the light-emitting part may further emit a second light toward a different direction from the detection site; the first sensor unit may further have a third reflector for reflecting the second light and leading the light to the detection site; and the first light-receiving part may receive the light including the biological information obtained from the second light being reflected by the detection site.

Thus, by the presence of the third reflector, the second light not directly reaching the detection site of the test subject (e.g., user) also reaches the detection site. In other words, the amount of light reaching the detection site is increased by way of the third reflector. Accordingly, the detecting accuracy of the biological information detector is improved.

According to a fourth aspect of the present invention, the second sensor unit may further have a fourth reflector for reflecting a part of the light including the second noise information and suppressing the light including the second noise information from reaching the second light-receiving part.

Because a first sensor unit has a light-emitting part (and a third reflector), a part of the external light transmitted through the test subject is blocked or reflected by the light-emitting part (or the third reflector), and is suppressed from reaching the first reflecting part. That is, the amount of external light reaching the first reflecting part is made less than the amount of external light reaching the second reflecting part, by the amount blocked or reflected by the light-emitting part (or the third reflector). Therefore, by the presence of the fourth reflector (dummy reflector), the part of the external light transmitted through the test subject is suppressed from reaching the second reflecting part, by being blocked or reflected by the fourth reflector. The difference between the amount of external light received by the second light-receiving part and the amount of external light received by the first light-receiving part can thus be reduced. The first noise information detected by the first sensor unit and the second noise information detected by the second sensor unit can thereby be more accurately corrected or cancelled, whereby the detecting accuracy of the biological information detector is further improved.

According to a fifth aspect of the present invention: the first sensor unit may further have: a wiring to the light-emitting part; and a wiring to the first light-receiving part; and the second sensor unit may further have: a wiring to the second light-receiving part; and a pseudo-wiring for suppressing the light including the second noise information from reaching the second light-receiving part.

Because the first sensor unit has a first wiring to the light-emitting part, the amount of external light transmitted through the test subject is blocked or reflected by the wiring to the light-emitting part, and is suppressed from reaching the first reflecting part. Specifically, the amount of external light reaching the first reflecting part is made less than the amount of external light reaching the second reflecting part, by the amount blocked or reflected by the wiring to the light-emitting part. Therefore, by the presence of the pseudo-wiring, the part of the external light transmitted through the test subject is suppressed from reaching the second reflecting part, by being blocked or reflected by the pseudo-wiring. The difference between the amount of external light received by the second light-receiving part and the amount of external light received by the first light-receiving part can thus be reduced. The first noise information detected by the first sensor unit and the second noise information detected by the second sensor unit can thereby be more accurately corrected or cancelled, whereby the detecting accuracy of the biological information detector is further improved.

According to a sixth aspect of the present invention: the first reflecting part may be formed as a spherical surface or a parabolic surface; the second reflecting part may be formed as a spherical surface or a parabolic surface; and a relation $\Delta hc > \Delta h$ may be satisfied, where $\Delta h$ is a distance between a light-receiving surface of the first light-receiving part and a center of an arc defining the spherical surface of the first reflecting part or a focus of a parabola defining the parabolic surface of the first reflecting part, and $\Delta hc$ is a distance between a light-receiving surface of the second light-receiving part and a center of an arc defining the spherical surface of the second reflecting part or a focus of a parabola defining the parabolic surface of the second reflecting part.

Thus, by satisfying the relation $\Delta hc > \Delta h$, the difference between the amount of external light received by the second light-receiving part and the amount of external light received by the first light-receiving part can be reduced. The first noise information detected by the first sensor unit and the second noise information detected by the second sensor unit can be more accurately corrected or cancelled, whereby the detecting accuracy of the biological information detector is further improved.

A seventh aspect of the present invention relates to a biological information measurement device, characterized in comprising: a biological information detector described above; and a biological information measurement unit for measuring the biological information on the basis of signals generated in the first light-receiving part and signals generated in the second light-receiving part.

According to an eighth aspect of the present invention, the measurement accuracy of the biological information measurement device can be improved by using a biological information detector having improved detecting accuracy.

According to a ninth aspect of the present invention, the biological information may be a pulse count.

A biological information measurement device having improved measurement accuracy can thus be applied to a pulsometer.

BRIEF DESCRIPTION OF THE DRAWINGS

FIG. 4 is another example of the configuration of the first sensor unit;

FIGS. 5(A) to (C) are examples of the configuration of the first detecting reflector;

FIGS. 6(A) and (B) are examples of the external appearance of the first detecting reflector and the detecting light-emitting part 14-1;

DESCRIPTION OF EXEMPLARY EMBODIMENTS

The present embodiment is described below. The present embodiment is not to be unduly construed as a limitation of the specifics of the present invention as described in the claims. Also, not all of the configurations described in the present embodiment are necessary configuration elements of the present invention.

1. Biological Information Detector

Figure 1:
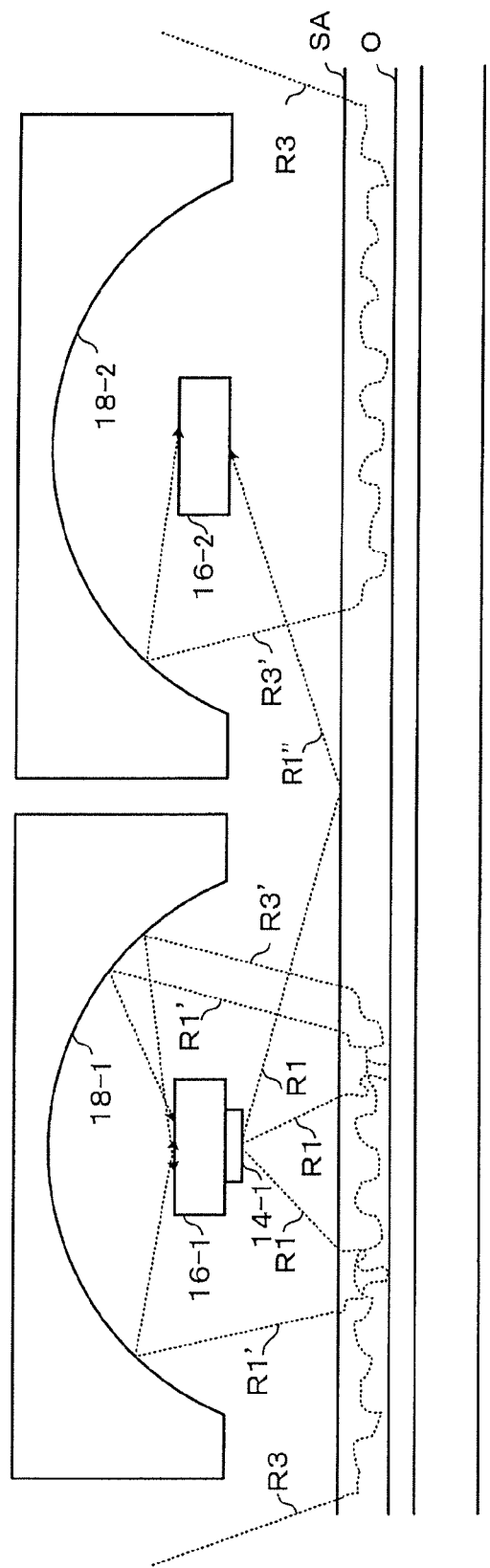
FIG. 1 is an example of the configuration of the biological information detector of the present embodiment.

FIG. 1 is an example of the configuration of the biological information detector of the present embodiment. As illustrated in FIG. 1, the biological information detector includes a first sensor unit (corresponding to the first sensor unit) and a correcting sensor unit (corresponding to the second sensor unit). The first sensor unit has a detecting light-emitting part 14-1 (corresponding to the light-emitting part), a detecting light-receiving part 16-1 (corresponding to the first light-receiving part), and a detecting reflector 18-1 (corresponding to the first reflecting part). The correcting sensor unit has a correcting light-receiving part 16-2 (corresponding to the second light-receiving part), and a correcting reflector 18-2 (corresponding to the second reflecting part).

In FIG. 1, the detecting light-emitting part 14-1 emits light R1 toward a detection site O. The detecting light-receiving part 16-1 receives light R1' containing biological information obtained by the light R1 (reflected light) emitted toward the detection site O being reflected by the detection site O, and light R3' (transmitted light: noise) containing first noise information obtained from external light R3 being transmitted through a test subject (e.g., user). The detecting reflector 18-1 reflects the light R1' (reflected light) containing the biological information from the detection site O and the light R3' (transmitted light) containing the first noise information from inside the test subject, and leads the light to the detecting light-receiving part 16-1. The detecting reflector 18-1 may have a reflecting surface on a domed surface provided on an optical path between the detecting light-emitting part 14-1 and the detecting light-receiving part 16-1. The first sensor unit is used for detecting composite information including the biological information in the detection site of the test subject and the first noise information originating in the external light R3.

The correcting light-receiving part 16-2 receives the light R3' (transmitted light: noise) containing second noise information obtained from the external light R3 being transmitted through the test subject. The correcting reflector 18-2 reflects the light R3' containing the second noise information from inside the test subject, and leads the light to the correcting light-receiving part 16-2. The correcting reflector 18-2 may have a reflecting surface on a domed surface provided on an optical path between the detection site O and the correcting light-receiving part 16-2. The correcting sensor unit is used for detecting the second noise information originating in the external light R3. The correcting sensor unit does not necessarily require a light-emitting part such as the detecting light-emitting part 14-1 of the first sensor unit.

In the example in FIG. 1, the detection site O (e.g., a blood vessel) is inside the test subject. The first light R1 enters into the test subject, and is diffused or scattered in the epidermis, dermis, and hypodermis. The first light R1 then reaches the detection site O, and is reflected by the detection site O. The light R1' reflected by the detection site O is diffused or scattered by the hypodermis, dermis, and epidermis, and proceeds toward the detecting reflector 18-1. The first light R1 is partially absorbed by the blood vessel. Accordingly, the absorption rate in the blood vessel changes due to an effect of the pulse, and the amount of light R1' reflected by the detection site O also changes. The biological information (e.g., the pulse count) thus is reflected in the light R1' reflected by the detection site O.

On the other hand, the external light R3 (e.g., sunlight) is diffused or scattered inside the test subject. The transmitted light R3' transmitted through the test subject without reaching the detection site O proceeds toward the detecting reflector 18-1 or the correcting reflector 18-2. Accordingly, the biological information (pulse count) is not reflected in the transmitted light R3' transmitted through the test subject. The external light R3 is also diffused or scattered inside the test subject, for example, in locations where tendons, bones, or other obstructions are not present, and noise information is therefore reflected in the transmitted light R3' transmitted through the test subject.

In the example in FIG. 1, the first light R1 is reflected also by an outer surface (skin surface) SA of the test subject. In the case when the detection site O is inside the test subject, the biological information (pulse count) is not reflected in the light R1" (directly reflected light) reflected by the outer surface SA of the test subject. In the example in FIG. 1, the reflected light R1" (in the broad sense, noise) is prevented from reaching the correcting light-receiving part 16-2.

The configuration example of the biological information detector is not limited by FIG. 1, and the shape, or the like, of a part (e.g., detecting reflector 18-1 or correcting reflector 18-2) of the configuration example may be modified. The biological information may also be blood oxygen saturation, body temperature, heart rate, or the like, and the detection site may also be on the outer surface SA of the test subject. In FIG. 1, the first light R1 is depicted as three lines, but the detecting light-emitting part 14-1 in fact emits a large number of lights in various directions. The external light R3 is also depicted as two lights, but a large number of external lights in fact enter into the test subject from various directions, and a large number of transmitted lights R3 transmitted through the test subject in fact proceed toward the biological information detector as a result.

In FIG. 1, the reflected light R1' (valid light) reflected by the detection site O reaches the detecting light-receiving part 16-1 by way of the detecting reflector 18-1, but is suppressed from reaching the correcting light-receiving part 16-2.

Accordingly, the detecting light-receiving part 16-1 efficiently receives the light emitted by the detecting light-emitting part 14-1, but the correcting light-receiving part 16-2 receives almost no light emitted by the detecting light-emitting part 14-1. The external light R3 has a wavelength of 700 [nm] to 1100 [nm] that is easily transmitted through the so-called "biological window," and the transmitted light R3' (in the broad sense, noise) transmitted through the test subject reaches the detecting reflector 18-1 and the correcting reflector 18-2. The correcting light-receiving part 16-2 thus is independent from the detecting light-receiving part 16-1, and can efficiently sense the second noise information originating in the external light R3 transmitted through the test subject. Here, the transmitted light R1' containing the first noise information obtained from the external light R3 being transmitted through the test subject also is received by the detecting light-receiving part 16-1, but the biological information in the detection site O can be efficiently detected upon correction or cancellation of the first noise information by the second noise information. The detecting accuracy (S/N ratio) of the biological information detector is thereby improved. In the case when the reflecting surface of the detecting reflector 18-1 is a domed surface, the reflected light R1' reflected by the detection site O is more easily condensed on the detecting light-receiving part 16-1, and the reflected light R1' can be made less likely to reach the correcting light-receiving part 16-2 to that extent. In such case, the detecting accuracy (S/N ratio) of the biological information detector is further increased.

Patent Citation 1 discloses a configuration (photodiode 33) corresponding to the correcting light-receiving part 16-2, but the photodiode 33 barely receives light emitted by an LED 31. Patent Citation 1 also does not disclose a configuration corresponding to the correcting reflector 18-1. The photodiode 33 thus is not independent of the photodiode 32, and is not capable of efficiently detecting just the noise information originating in the external light. In other words, increasing the efficiency of the photodiode 33 in FIG. 4 of Patent Citation 1 is not known to persons skilled in the art at the time of filing.

For example, the detecting light-emitting part 14-1 is an LED. For example, the maximum value (in the broad sense, peak value) of intensity of light emitted by an LED is in a wavelength range from 425 [nm] to 625 [nm]. For example, green light is emitted. For example, the thickness of the detecting light-emitting part 14-1 is 20 [μm] to 1000 [μm]. For example, the detecting light-receiving part 16-1 is a photodiode, and generally can be configured with a Si photodiode. For example, the thickness of the detecting light-receiving part 16-1 is 20 [μm] to 1000 [μm]. For example, the maximum value (in the broad sense, peak value) of sensitivity to light received by a Si photodiode is in a wavelength range from 800 [nm] to 1000 [nm]. Preferably, the detecting light-receiving part 16-1 is configured with a GaAsP photodiode, and for example, the maximum value (in the broad sense, peak value) of sensitivity to light received by a GaAsP photodiode is in a wavelength range from 550 [nm] to 650 [nm]. A biological substance (water or hemoglobin) easily transmits infrared radiation included in a range of 700 [nm] to 1100 [nm], and a detecting light-receiving part configured with a GaAsP photodiode is therefore more capable of reducing the noise component originating in the external light, for example, compared with a light-receiving part 16-1 configured with a Si photodiode.

For example, the correcting light-receiving part 16-2 is a photodiode. The second noise information contained in the light received by the correcting light-receiving part 16-2 is preferably equal to the first noise information contained in the light received by the detecting light-receiving part 16-1, and therefore the correcting light-receiving part 16-2 is preferably the same photodiode as the detecting light-receiving part 16-1.

Figure 2:
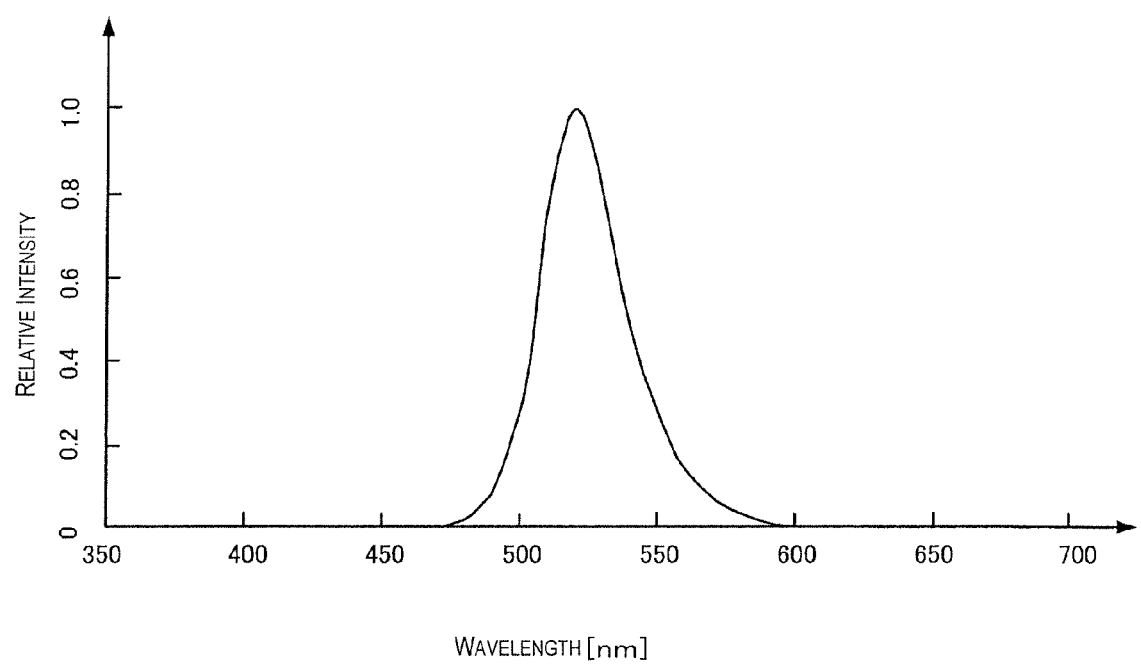
FIG. 2 is an example of the intensity characteristics of light emitted by the detecting light-emitting part.

FIG. 2 illustrates an example of the intensity characteristics of light emitted by the detecting light-emitting part 14-1. In the example in FIG. 2, the maximum value of intensity is indicated for light having a wavelength of 520 [nm], and the intensity of light of other wavelengths is normalized by that intensity. In the example in FIG. 2, the wavelength range of light emitted by the detecting light-emitting part 14-1 is from 470 [nm] to 600 [nm].

Figure 3:
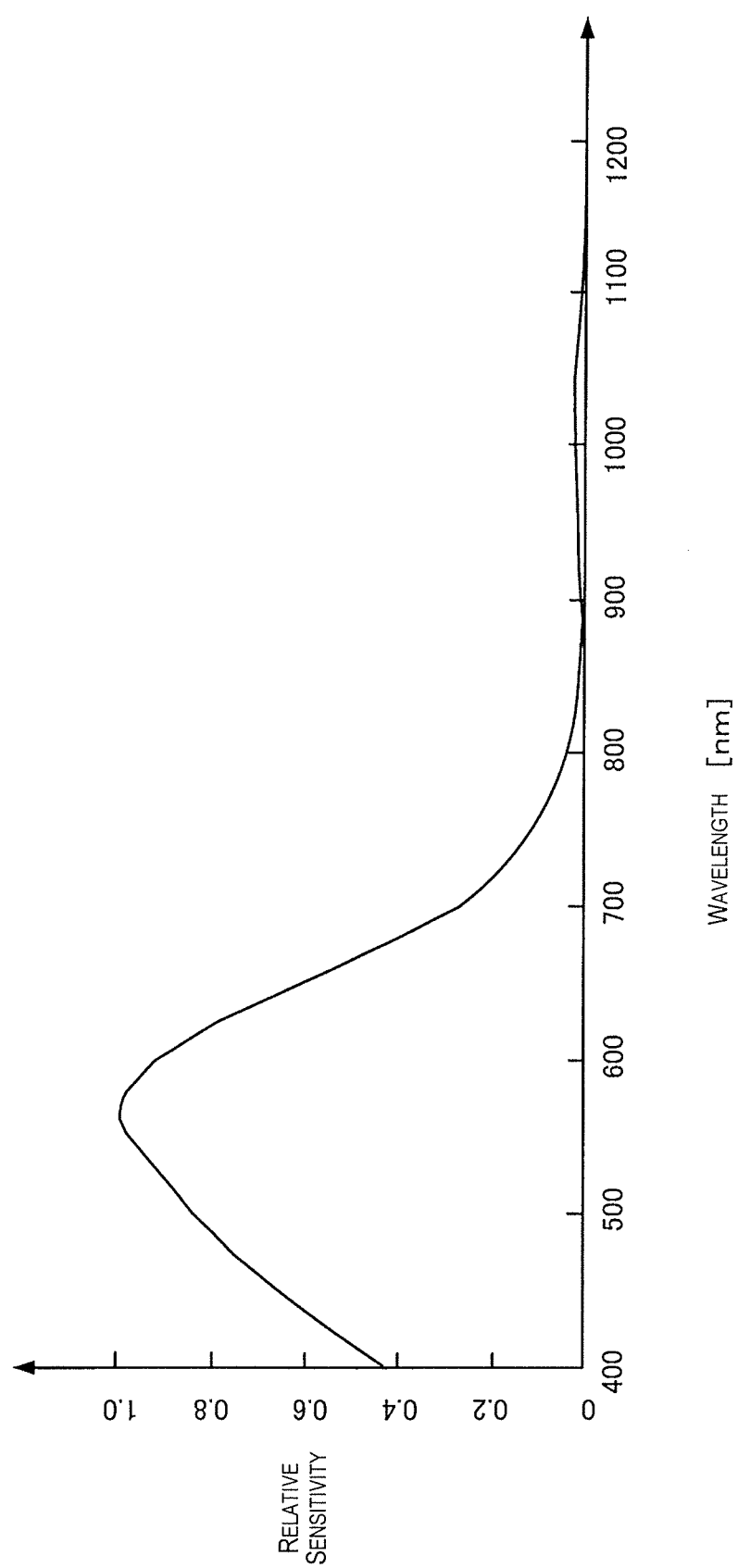
FIG. 3 is an example of the sensitivity characteristics to light received by the detecting light-receiving part.

FIG. 3 illustrates an example of the sensitivity characteristics to light received by the detecting light-receiving part 16-1. In the example in FIG. 3, the maximum value of sensitivity is indicated for light having a wavelength of 565 [nm], and the sensitivity to light in other wavelengths is normalized by that sensitivity. The maximum value of sensitivity to wavelength of light received by the detecting light-receiving part 16-1 illustrated in FIG. 3 is within the wavelength range of light emitted by the detecting light-emitting part 14-1 illustrated in FIG. 2, but is not within the range of 700 [nm] to 1100 [nm] referred to as the "biological window." In the example in FIG. 3, the sensitivity to infrared radiation included in the range from 700 [nm] to 1100 [nm] is set to a relative sensitivity of 0.3 (30[%]) or lower. The maximum value (e.g., 565 [nm]) of sensitivity to wavelength of light received by the detecting light-receiving part 16-1 is preferably closer to the maximum value (520 [nm]) of the intensity of the wavelength of light emitted by the light-emitting part 14 from the 700 [nm] lower limit of the biological window.

FIG. 4 illustrates another example of the configuration of the first sensor unit. As illustrated in FIG. 4, the first sensor unit of the biological information detector may include a detecting reflector 42-1 (corresponding to the third reflector) for reflecting light. Identical reference numerals are assigned to identical configurations with the above configuration example, and the description of the correcting sensor unit is omitted. In the following description, the detecting reflector 42-1 is referred to as "first detecting reflector," and the detecting reflector 18-1 in FIG. 1 is referred to as "second detecting reflector."

In the example in FIG. 4, the first sensor unit of the biological information detector includes a detecting light-emitting part 14-1, a first detecting reflector 42-1, a detecting light-receiving part 16-1, and a second detecting reflector 18-1. The detecting light-emitting part 14-1 emits a first light R1 toward the detection site O of the test subject (user), and a second light R2 toward a different direction (the first detecting reflector 42-1) than the detection site O. The first detecting reflector 42-1 reflects the second light R2 and leads the light to the detection site O. The detecting light-receiving part 16-1 receives lights R1' and R2' (reflected lights) containing the biological information obtained from the first light R1 and the second light R2 being reflected by the detection site O. The second detecting reflector 18-1 reflects the lights R1' and R2' (reflected lights) containing the biological information from the detection site O and leads the lights to the detecting light-receiving part 16-1. By the presence of the first detecting reflector 42-1, the second light R2 not directly reaching the detection site O of the test subject (user) also reaches the detection site O. In other words, the amount of light reaching the detection site O is increased by way of the first detecting reflector 42-1. Accordingly, the detecting accuracy (SN ratio) of the biological information detector is improved.

In the example in FIG. 4, the second light R2 enters into the test subject, and the light R2' reflected by the detection site O proceeds toward the second detecting reflector 18-1. The biological information (pulse count) is reflected also in the light R2' reflected by the detection site O. In the example in FIG. 4, the first light R1 is partially reflected by the outer surface (skin surface) SA of the test subject. In the case when the detection site O is inside the test subject, the biological information (pulse count) is not reflected in the light R1" (directly reflected light) reflected by the outer surface SA of the test subject. In the example in FIG. 4, the transmitted light R3' transmitted through the test subject proceeds toward the same direction as the reflected light R1".

In the example in FIG. 4, the detecting light-emitting part 14-1 may have a first light-emitting surface 14-1A for emitting the first light R1, opposed to the detection site O. The detecting light-emitting part 14-1 may also have a second light-emitting surface 14-1B for emitting the second light R2, being to the side of the first light-emitting surface 14-1A. In this case, the first detecting reflector 42-1 may have a wall part surrounding the second light-emitting surface 14-1B, and this wall part may have a first reflecting surface (corresponding to the reference numeral 42B indicated in FIGS. 5(A) to (C)) for reflecting the second light R2 toward the detection site O. The second light R2 is not necessarily emitted from the second light-emitting surface 14-1B. The point is that the first reflecting surface (reference numeral 42B in FIGS. 5(A) to (C)) reflects the light (second light R2) other than the light directly emitted toward the detection site O from the detecting light-emitting part 14-1, and leads the light to the detection site O.

The wall part of the first detecting reflector 42 may further have a second reflecting surface (corresponding to the reference numeral 42C indicated in FIGS. 5(A) to (C) for reflecting light (invalid light: noise) not containing the biological information, reflected by the outer surface of the test subject, and thereby suppressing the light not including the biological information from being input to the detecting light-receiving part 16-1. The second reflecting surface (42C) can reflect also the transmitted light R3' and suppressing input to the detecting light-receiving part 16-1. The configuration example of the first sensor unit of the biological information detector is not limited by FIG. 4, and the shape, or the like, of a part (e.g., first detecting reflector 42-1) of the configuration example may be modified.

FIGS. 5(A), (B), and (C) illustrate an example of the configuration of the first detecting reflector 42-1 in FIG. 4. As illustrated in FIG. 5(A), the first detecting reflector 42-1 may have a support part 42A for supporting the detecting light-emitting part 14-1, and an inner wall surface 42B and a top surface 42C of a wall part surrounding the second light-emitting surface 42B of the detecting light-emitting part 14-1. In FIGS. 5(A) to (C), the detecting light-emitting part 14-1 is omitted. In the example in FIG. 5(A), the first detecting reflector 42-1 can reflect the second light R2 on the inner wall surface 42B to the detection site O (see FIG. 4), and has a first reflecting surface on the inner wall surface 42B. For example, the thickness of the support part 42A is 50 [μm] to 1000 [μm], and for example, the thickness of the wall part (42C) is 100 [μm] to 1000 [μm].

In the example in FIG. 5(A), the inner wall surface 42B has an inclined surface (42B) that is displaced toward the side of the detection site O in a height direction (a direction perpendicular to a first direction) while going away from the center of the first detecting reflector 42 in a width direction (the first direction) in sectional view. The inclined surface (42B) in FIG. 5(A) is formed as an inclined plane, but may be formed as a curved surface or other inclined surface. The inner wall surface 42B may be formed as a plurality of inclined planes having different angles of inclination, or may be formed as curved surfaces having a plurality of curvatures. In the case when the inner wall surface 42B of the first detecting reflector 42-1 has an inclined surface, the inner wall surface 42B of the first detecting reflector 42-1 can reflect the second light R2 toward the detection site O. In other words, the inclined surface of the inner wall surface 42B of the first detecting reflector 42-1 may be considered as a first reflecting surface for increasing the directionality of the detecting light-emitting part 14-1. In this case, the amount of light reaching the detection site O is further increased. The top surface 42C in FIGS. 5(A) and (C) may be omitted, for example, as illustrated in FIG. 5(B). In the case when the first detecting reflector 42-1 has a top surface 42C, the light R1" (directly reflected light) reflected by the outer surface SA of the test subject can be reflected to the detection site or the periphery thereof, and the reflected light R1" can be suppressed from reaching the detecting light-receiving part 16-1 (see FIG. 4). In short, the top surface 42C in FIGS. 5(A) and (C) can be considered as a second reflecting surface for reflecting the directly reflected light (in the broad sense, noise) that would reach the second detecting reflector 18-1 and the detecting light-receiving part 16-1, and reducing the noise. In FIGS. 5(A) to (C), the range indicated by the reference numeral 42D functions as a mirror surface.

In the example in FIG. 4, the first detecting reflector 42-1 may project toward the detection site O, for example, by a given height (e.g., $\Delta h1$=50 [μm] to 950 [μm]) with reference to the surface of the detecting light-emitting part 14-1 defining the shortest distance from the outer surface SA of the test subject. In other words, a gap (e.g., $\Delta h2=\Delta h0-\Delta h1$=200 [μm] to 1200 [μm]) between the first detecting reflector 42-1 and the outer surface SA of the test subject can be made smaller than a gap (e.g., $\Delta h0=\Delta h1+\Delta h2$) being between the detecting light-emitting part 14-1 and the outer surface SA of the test subject. Accordingly, the area of the reflecting surface (42B) of the first detecting reflector 42-1 can be increased, for example, by the presence of the protruding amount $\Delta h1$ from the detecting light-emitting part 14-1, and the amount of light reaching the detection site O can be increased. An optical path for the light reflected on the detection site O to reach the second detecting reflector 18-1 from the detection site O can be secured by the presence of the gap $\Delta h2$ between the first detecting reflector 42-1 and the outer surface SA of the test subject. In the case when the first detecting reflector 42-1 has a second reflecting surface (92C), the amounts of light (valid light) containing the biological information and light (invalid light: noise) not containing the biological information input to the detecting light-receiving part 16-1 can be respectively adjusted by adjusting $\Delta h1$ and $\Delta h2$, whereby the S/N can be further improved.

FIGS. 6(A) and (B) illustrate an example of the external appearance in plan view of the first detecting reflector 42-1 and the detecting light-emitting part 14-1 in FIG. 4. In the example in FIG. 6(A), the outer perimeter of the first detecting reflector 42-1 expresses a circle in plan view (e.g., on the side of the detection site O in FIG. 4), and, for example, the diameter of the circle is 200 [μm] to 11000 [μm]. In the example in FIG. 6(A), the wall part (42B) of the first detecting reflector 42-1 surrounds the detecting light-emitting part 14-1 (see FIGS. 4 and 5(A)). The outer perimeter of the first detecting reflector 42-1 expresses a quadrangular shape (in the narrow sense, a square shape) in plan view, for example, as illustrated in FIG. 6(B). In the example in FIGS. 6(A) and (B), the outer perimeter of the detecting light-emitting part 14-1 expresses a quadrangular shape (in the narrow sense, a square shape) in plan view (e.g., on the side of the detection site O in FIG. 4), and, for example, one side of the square shape is 100

[μm] to 10000 [μm]. The outer perimeter of the detecting light-emitting part 14-1 may describe a circular shape.

The first detecting reflector 42-1 itself is formed with metal, and the top surface is mirror-finished to have a reflective structure (in the narrow sense, a mirror-reflective structure). The first detecting reflector 42-1 may be formed, for example, with resin, and the top surface may be mirror-finished. Specifically, for example, a metal undercoating of the first detecting reflector 42-1 is prepared, and then, for example, the top surface is plated. Or, for example, a thermoplastic resin is filled into a mold (not illustrated) of the first detecting reflector 42-1, and then, for example, a metal film is vapor-deposited on the top surface.

In the example in FIGS. 6(A) and (B), the first detecting reflector 42-1 is exposed in a region (a part of the support part 42A, and the inner wall surface 42B and top surface 42C of the wall part) other than the region where the detecting light-emitting part 14-1 is directly supported, in plan view (e.g., on the side of the detection site O in FIG. 4). This exposed region is indicated as the mirror-surface part 42D in the example in FIG. 5(A). In the example in FIG. 5(A), the dotted line indicating the mirror surface part 42D is positioned on the inside of the first detecting reflector 42-1, but the mirror surface part 42D in fact is formed on the top surface of the first detecting reflector 42-1.

In the example in FIGS. 5(A), (B), and (C), the mirror surface part 42D preferably has high reflectivity. For example, the reflectivity of the mirror surface part 42D is 80% to 90% or higher. The mirror surface part 42D may be formed only on the inclined surface of the inner wall surface 42B. In the case when the mirror surface 42D is formed not only on the inclined surface, but also on the support part 42A, the directionality of the detecting light-emitting part 14 becomes even higher. In the case when the mirror surface part 42D is formed on the top surface 42C, the first detecting reflector 42-1 can reflect the light R1" (directly reflected light: invalid light) reflected by the outer surface SA of the test subject to the detection site O or the periphery thereof, and the reflected light R1" can be suppressed from reaching the second detecting reflector 18-1 and the detecting light-receiving part 16-1, for example, as illustrated in FIG. 4. Because the directionality of the detecting light-emitting part 14-1 becomes higher, and because the directly reflected light (in the broad sense, noise) is reduced, the detecting accuracy of the biological information detector is improved.

In the example in FIG. 4, the transmitted light R3' transmitted through the test subject proceeds in the same direction as the reflected light R1". That is, by the presence of the first detecting reflector 42-1, the transmitted light R3' transmitted through the test subject is suppressed from reaching the second detecting reflector 18-1. Likewise, by the presence of the detecting light-emitting part 14-1, the transmitted light R3' transmitted through the test subject is suppressed from reaching the second detecting reflector 18-1. For example, in the case when the detecting light-emitting part 14-1 in FIG. 1 is as large as the first detecting reflector 42-1 in FIG. 4, the transmitted light R3' transmitted through the test subject is blocked or reflected by the detecting light-emitting part 14-1, and is suppressed from reaching the second detecting reflector 18-1. That is, the amount of transmitted light R3' (external light) reaching the second detecting reflector 18-1 is made less than the amount of transmitted light R3' (external light) reaching the correcting reflector, by the amount blocked or reflected by the detecting light-emitting part or the first detecting reflector.

Figure 8:
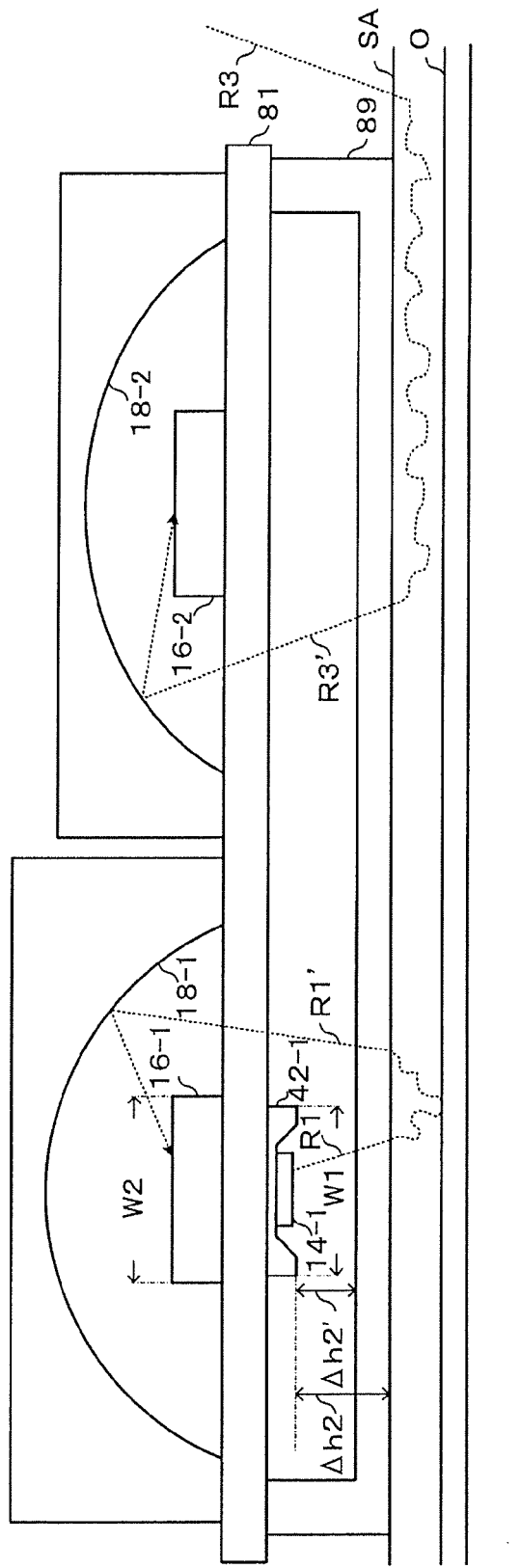
FIG. 8 is another example of the configuration of the biological information detector of the present embodiment.

Then, in the example in FIG. 1, a relation S2<S1 may be satisfied, for example, as in the example in FIG. 8, where S1 is the area of the reflecting surface of the detecting reflector 18-1 (second detecting reflector 18-1 in FIG. 4), and S2 is the area of the reflecting surface of the correcting reflector 18-2. In the case when the relation S2<S1 is satisfied, the transmitted light R3' transmitted through the test subject can be suppressed from reaching the correcting reflector 18-2, by the amount of reduction of area (S1−S2) of the reflecting surface of the correcting reflector 18-2. In other words, the amount of transmitted light R3' (external light) reaching the correcting reflector 18-2 is reduced by the amount of reduction of area (S1−S2) of the correcting reflector 18-2. In the case when S1=S2, as previously described, the amount of transmitted light R3' (external light) reaching the second detecting reflector 18-1 becomes less than the amount of transmitted light R3' (external light) reaching the correcting reflector 18-2, and therefore the difference between the amount of transmitted light R3' (external light) received by the correcting light-receiving part 16-2 and the amount of transmitted light R3' (external light) received by the detecting light-receiving part 16-1 can be reduced by reducing the amount of transmitted light R3' (external light) reaching the correcting reflector 18-2.

Figure 7:
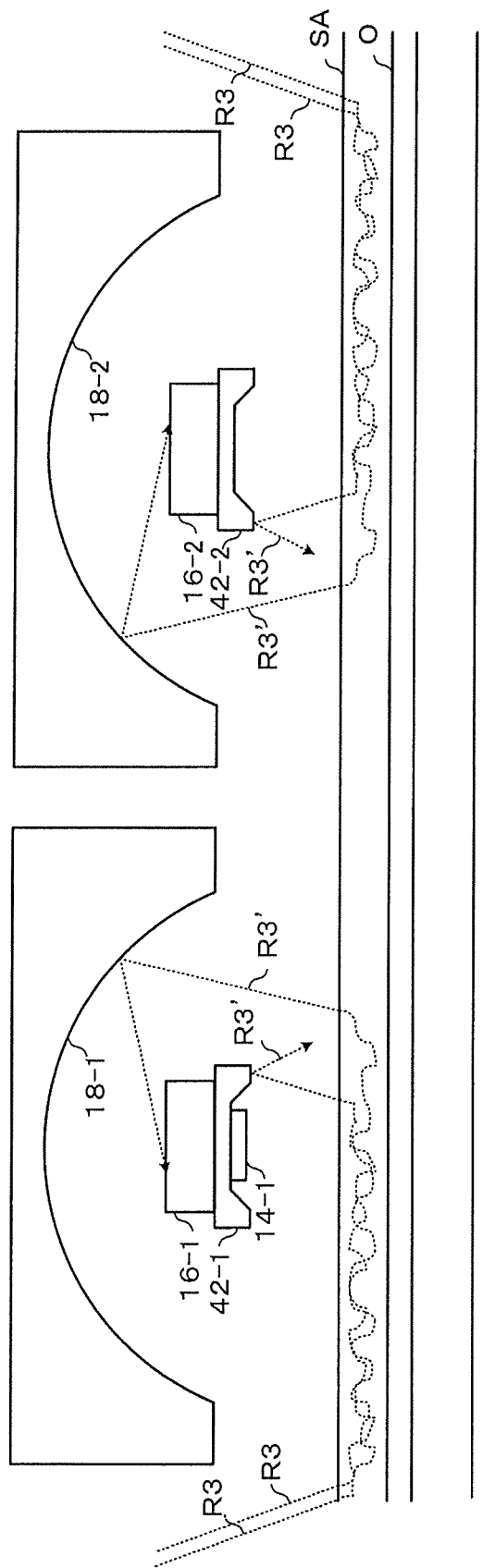
FIG. 7 is another example of the configuration of the biological information detector of the present embodiment.

FIG. 7 illustrates another example of the configuration of the biological information detector of the present embodiment. As illustrated in FIG. 7, the correcting sensor unit of the biological information detector may have a dummy reflector 42-2 (corresponding to the fourth reflector) for reflecting a part of the transmitted light R3' (external light) transmitted through the test subject and suppressing the transmitted light R3' from reaching the correcting light-receiving part 16-2. Identical reference numerals are assigned to identical configurations with the above-described configuration example, and the description is omitted. The dummy reflector 42-2 is referred to as "first correcting reflector," and the correcting reflector 18-2 is referred to as "second correcting reflector." In the example in FIG. 7, because the correcting sensor unit does not have a light-emitting part such as the detecting light-emitting part 14-1 of the first sensor unit, the dummy reflector 42-2 (first correcting reflector) is originally not required. However, by the presence of the dummy reflector 42-2 (first correcting reflector), a part of the transmitted light R3' (external light) transmitted through the test subject is suppressed from reaching the correcting reflector 18-2 (second correcting reflector). In other words, even in the case when the area (S1) of the reflecting surface of the detecting reflector 18-1 (second detecting reflector) is equal to the area (S2) of the correcting reflector 18-2 (second correcting reflector), the substantial area (S2') of the reflecting surface of the correcting reflector 18-2 (second correcting reflector) is reduced by the presence of the dummy reflector 42-2 (first correcting reflector). The difference between the amount of transmitted light R3' (external light) received by the correcting light-receiving part 16-2 and the amount of transmitted light R3' (external light) received by the detecting light-receiving part 16-1 can thus be reduced, or the difference can be brought substantially to zero.

FIG. 8 illustrates another example of the configuration of the biological information detector of the present embodiment. As illustrated in FIG. 8, the biological information detector may further include a substrate 81 having a first surface (e.g., top surface) and a second surface (e.g., bottom surface) opposed to the first surface. Identical reference numerals are assigned to identical configurations with the above-described configuration example, and the description is omitted. The detecting light-receiving part 16-1 and the correcting light-receiving part 16-2 are disposed on the first surface, and the first detecting reflector 42-1 is disposed on the second surface. A relation W1≤W2 may be satisfied, where W1 is the maximum length of the first detecting reflector 42-1 in a direction parallel to the first surface in sectional view, and W2 is the maximum length of the detecting light-receiving part 16 in that direction.

For example, the substrate 81 is made of a transparent material (e.g., polyimide), and transmits the reflected light R1' of the first light R1 emitted to the detection site O. The amount of light reaching the second detecting reflector 18-1 can be increased by setting the maximum length W1 of the first detecting reflector 42-1 to the maximum length W2 of the light-receiving part 16 or lower. In other words, the maximum length W1 of the first detecting reflector 42-1 can be set so that the reflected light R1' on the detection site O is not blocked or reflected by the first detecting reflector 42-1. For example, the thickness of the substrate 81 is 10 [μm] to 1000 [μm]. A wiring to the detecting light-emitting part 14-1, a wiring to the detecting light-receiving part 16-1, and a wiring to the correcting light-receiving part 16-2 may be formed on the board. For example, the substrate 81 is a printed board, but a printed board is not usually made of a transparent material. In other words, the present inventors ventured to constitute a printed board with a material that is at least transparent to the wavelength of light emission of the detecting light-emitting part 14-1.

In the example in FIG. 8, the second light R2 emitted by way of the first detecting reflector 42-1, the reflected light R2' on the detection site O, the light R1" (directly reflected light) reflected by the outer surface SA of the test subject, or the transmitted light R3' transmitted through the test subject are omitted (see FIG. 4). Persons skilled in the art should be able to easily understand the path for the second light R2, the correct path for the first light R1, or the correct path for the external light R3.

As illustrated in FIG. 8, the biological information detector may include a protector 89 for protecting the first detecting reflector 42-1 and the detecting light-emitting part 14-1. For example, the protector 89 is made of a transparent material (e.g., glass), and transmits the first light R1 emitted to the detection site O and the reflected light R1' of the first light R1. The protector 89 may ensure a gap (e.g., Δh2) is present between the first detecting reflector 42-1 and the detection site O. A gap (e.g., Δh2') between the first detecting reflector 42-1 and the protector 89 is also present. For example, the thickness of the protector 89 is 1 [μm] to 1000 [μm].

The substrate 81 is held between a composite reflector (second detecting reflector 18-1 and correcting reflector 18-2) and the protector 89. The detecting light-receiving part 16-1 is placed on the substrate 81 (in the narrow sense, on the first surface of the substrate 81) on the side of the second detecting reflector 18-1. The detecting light-emitting part 14-1 is placed on the substrate 81 (in the narrow sense, on the second surface of the substrate 81) on the side of the protector 89. The correcting light-receiving part 16-2 is placed on the substrate 81 (in the narrow sense, on the first surface of the substrate 81) on the side of the correcting reflector 18-2. Because the substrate 81 is held between the composite reflector (second detecting reflector 18-1 and correcting reflector 18-2) and the protector 89, even though the detecting light-emitting part 14-1, the detecting light-receiving part 16-1, and the correcting light-receiving part 16-2 are disposed on the substrate 81, there is no need to separately provide a mechanism for supporting the substrate 81 itself, and the number of parts is reduced. Because the substrate 81 is made of a material that is transparent to the wavelength of light emission, the substrate 81 can be disposed partway along the optical path from the detecting light-emitting part 14-1 to the detecting light-receiving part 16-1, and there is no need to store the substrate 81 in a position other than the optical path, for example, inside the second detecting reflector 18-1. A biological information detector that is easy to assemble can thus be provided.

In the example in FIG. 8, a relation S2<S1 may be satisfied, where S1 is the area of the reflecting surface of the second detecting reflector 18-1, and S2 is the area of the reflecting surface of the correcting reflector 18-2. By satisfying the relation S2<S1, the transmitted light R3' transmitted through the test subject is suppressed from reaching the correcting reflector 18-2, by the amount of reduction of area (S1−S2) of the reflecting surface of the correcting reflector 18-2. In the case when S1=S2, the amount of transmitted light R3' (external light) reaching the second detecting reflector 18-1 becomes less than the amount of transmitted light R3' (external light) reaching the correcting reflector 18-2, by the amount of transmitted light R3' (external light) blocked by the first detecting reflector 42-1 and the detecting light-emitting part 14-1. Therefore, the difference between the amount of transmitted light R3' (external light) received by the correcting light-receiving part 16-2 and the amount of transmitted light R3' (external light) received by the detecting light-receiving part 16-1 can be reduced by reducing the amount of transmitted light R3' (external light) reaching the correcting reflector 18-2.

Figure 9:
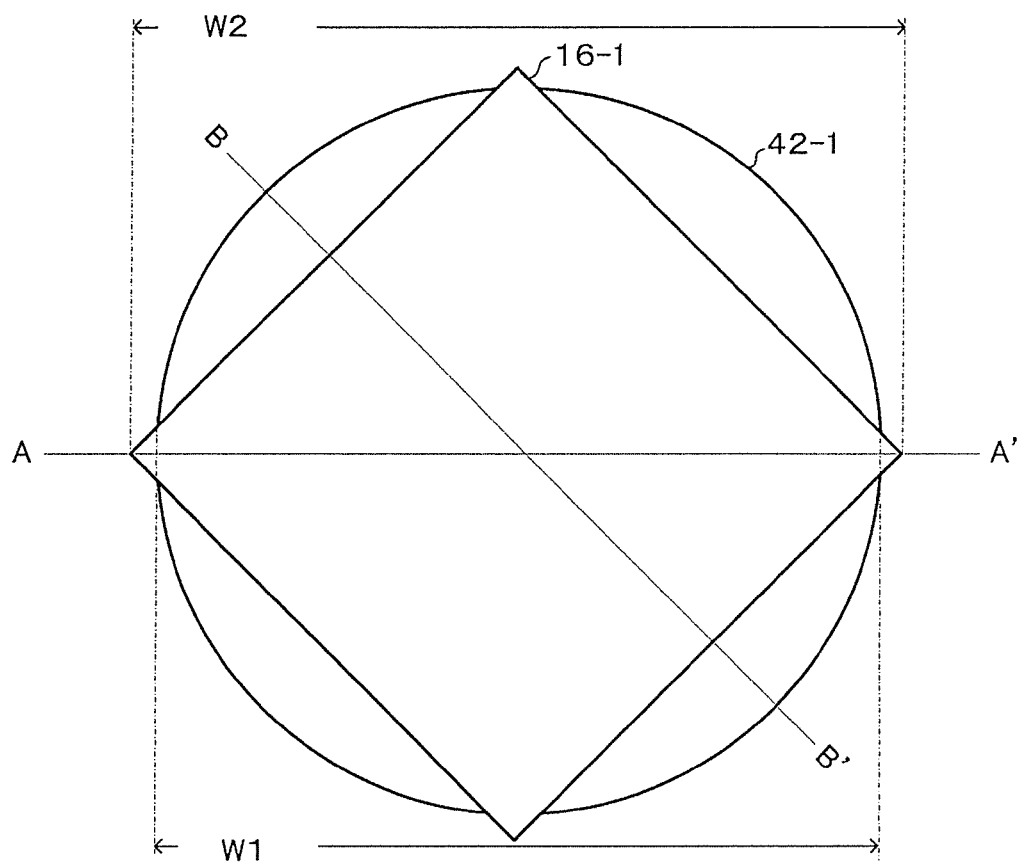
FIG. 9 is an example of the external appearance of the detecting light-receiving part.

FIG. 9 illustrates an example of the external appearance of the detecting light-receiving part 16-1 in FIG. 8. In the example in FIG. 9, the outer perimeter of the detecting light-receiving part 16-1 expresses a quadrangular shape (in the narrow sense, a square shape) in plan view (e.g., on the side of the second detecting reflector 18-1 in FIG. 8), and for example, one side of the square shape is 100 [μm] to 10000 [μm]. The outer perimeter of the first detecting reflector 42-1 describes a circle in plan view (e.g., on the side of the second detecting reflector 18-1 in FIG. 8). The outer perimeter of the first detecting reflector 42-1 may describe a quadrangular shape (in the narrow sense, a square shape) as in the example in FIG. 6(B). The outer perimeter of the detecting light-receiving part 16-1 may describe a circular shape.

In the example in FIG. 9, a relation W1≤W2 may be satisfied, where W1 is the maximum length of the first detecting reflector 42-1, and W2 is the maximum length of the detecting light-receiving part 16-1, as indicated by the line segment A-A'. The sectional view along the line segment A-A' in FIG. 9 corresponds to FIG. 8. The sectional view along the line segment B-B' in FIG. 9 is similar to FIG. 7, and the maximum length W1 of the first detecting reflector 42-1 is longer than the minimum length of the detecting light-receiving part 16-1. The maximum length W1 of the first detecting reflector 42-1 may be set to the minimum length of the detecting light-receiving part 16-1 or shorter, but the efficiency of the first detecting reflector 42-1 (in the broad sense, the efficiency of the detecting light-emitting part 14-1) is reduced. In the example in FIG. 9, the maximum length W1 of the first detecting reflector 42-1 is set to maximum length W2 of the detecting light-receiving part 16-1 or shorter, and the maximum length W1 of the first detecting reflector 42-1 is set larger than the minimum length of the detecting light-receiving part 16-1, so that the reflected light R1' is not blocked or reflected while the efficiency of the detecting light-emitting part 14-1 is maintained.

Figure 10:
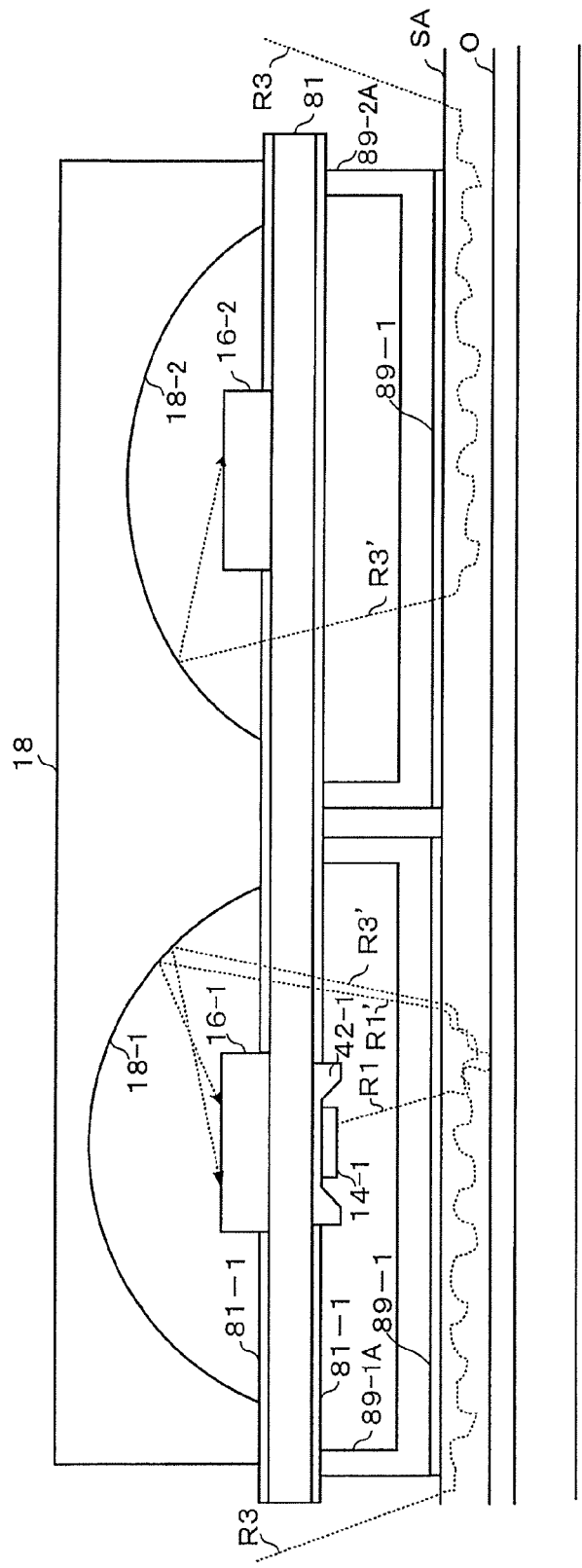
FIG. 10 is another example of the configuration of the biological information detector of the present embodiment.

FIG. 10 illustrates another example of the configuration of the biological information detector of the present embodiment. As illustrated in FIG. 10, a light-transmitting film 81-1 may be formed on the first surface (e.g., top surface) of the substrate 81, and on the second surface (e.g., bottom surface) opposed to the first surface. Identical reference numerals are assigned to identical configurations with the above-described configuration example, and the description is omitted. The light-transmitting film 81-1 may be formed only on the first surface or may be formed only on the second surface. In the example in FIG. 10, the light-transmitting film 81-1 is formed on a light-transmitting region of the substrate 81 where the detecting light-emitting part 14-1 (in the narrow sense, the first detecting reflector 42-1), the detecting light-receiving part 16-1, and the correcting light-receiving part 16-2 are not disposed. For example, the light-transmitting film 81-1 may be constituted with a solder resist (in the broad sense, a resist). The detecting light-emitting part (in the narrow sense, the first detecting reflector 42-1), the detecting light-receiving part 16-1, the correcting light-receiving part 16-2, and the like, may be disposed after the light-transmitting film 81-1 is formed on the substrate 81. In the example in FIG. 10, the second detecting reflector 18-1 and the correcting reflector 18-2 are formed as a single composite reflector.

In the example in FIG. 10, the wiring to the detecting light-emitting part 14-1, the wiring to the detecting light-receiving part 16-1, and the wiring to the correcting light-receiving part 16-2 are omitted, but the first surface and the second surface of the substrate 81 can be rough surface-finished so that the wirings on the substrate 81 will not detach. Accordingly, by forming the light-transmitting film 81-1 on the first surface and the second surface, the rough surface on the surface of the substrate 81 is embedded in the light-transmitting film, and the overall flatness of the substrate 81 is improved. In other words, because the light-transmitting film 81-1 on the substrate 81 is flat, the diffusion of light on the rough surface on the surface of the substrate 81 when the light is transmitted through the substrate 81 can be reduced. In other words, the transmittance of the substrate 81 is improved by the presence of the light-transmitting film 81-1. Accordingly, the amount of light reaching the detecting light-receiving part 16-1 and the correcting light-receiving part 16-2 is increased, and the detecting accuracy of the biological information detector is improved.

The refractive index of the light-transmitting film is preferably between the refractive index of air and the refractive index of the board. The refractive index of the light-transmitting film 81-1 is preferably closer to the refractive index of the substrate 81 than the refractive index of air. In such case, the reflection of light at the interface can be reduced.

The biological information detector may further include an infrared-cutting filter 89-1. An infrared-cutting filter 89-1 is disposed on the optical path from the detecting light-emitting part 14-1 to the detecting light-receiving part 16-1. An infrared-cutting filter 89-1 is likewise disposed also on the optical path from the external light to the correcting light-receiving part 16-2. In the example in FIG. 10, an infrared-cutting filter 89-1 is formed on the contact surface of a detection protector 89-1A and on the contact surface of a correction protector 89-2A. In the example in FIG. 8, the contact surface of the detection protector 89-1A, and the correction protector 89-2A are formed as a single protector 89 (composite protector). The infrared-cutting filter 89-1 in FIG. 10 may be formed on the contact surface of the single protector 89. For example, the infrared-cutting filter 89-1 may be constituted by coating the contact surface of the detection protector 89-1A and the contact surface of the correction protector 89-2A with an infrared-absorbing material. In the case when the detection protector 89-1A and the correction protector 89-2A (single protector 89) are made of glass, the detection protector 89-1A and the correction protector 89-2A (single protector 89) having the infrared-cutting filter 89-1 may be referred to as "infrared-cutting glass." The infrared-cutting filter 89-1 may be formed on the entire surface on the outside of the detection protector 89-1A and on the entire surface on the outside of the correction protector 89-2A, rather than only on the contact surface of the detection protector 89-1A and the contact surface of the correction protector 89-2A. The infrared-cutting filter 89-1 may be formed on the entire surface on the inside of the detection protector 89-1A and on the entire surface on the inside of the correction protector 89-2A. Or, the infrared-cutting filter 89-1 may be formed on the surface of the substrate 81, the detecting light-receiving part 16-1 and on the surface of the correcting light-receiving part 16-2, instead of on the contact surface of the detection protector 89-1A and the contact surface of the correction protector 89-2A. Because a biological substance (water or hemoglobin) easily transmits infrared light, the noise component originating in the external light can be reduced by an infrared-cutting filter 89-1 disposed on the optical path from the detecting light-emitting part 14-1 to the detecting light-receiving part 16-1. In the correcting sensor unit, just as in the first sensor unit, the noise component originating in the external light can be reduced by disposing an infrared-cutting filter 89-1 on the optical path from the external light to the correcting light-receiving part 16-2.

Figure 11:
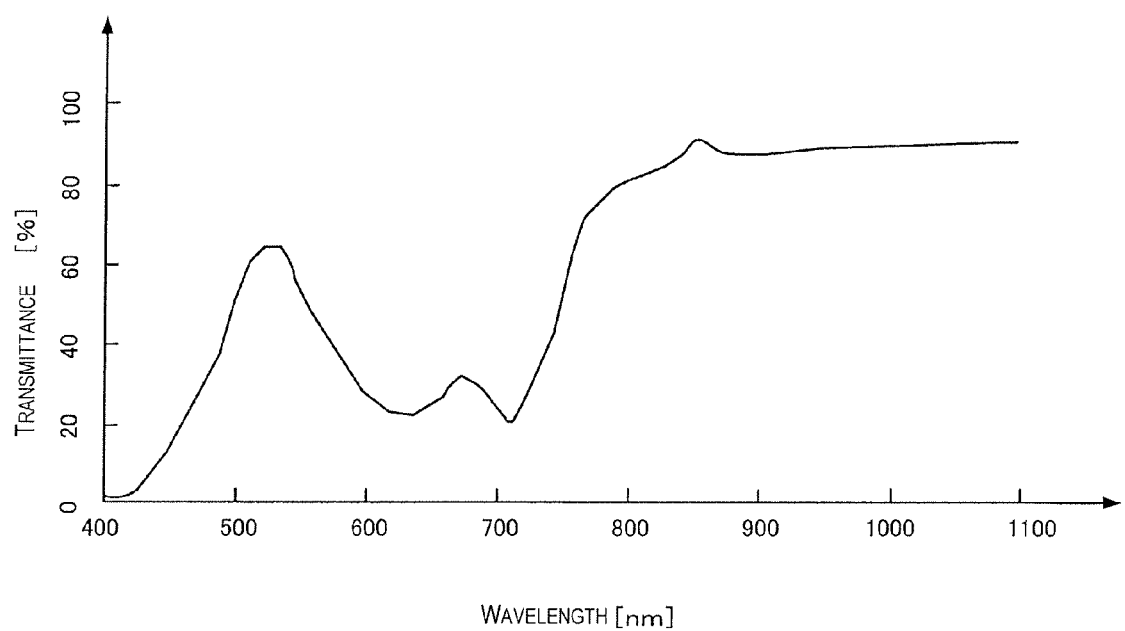
FIG. 11 is an example of the transmission characteristics of light passing through a board coated with a light-transmitting film.

FIG. 11 illustrates an example of the transmission characteristics of light through a substrate 81 coated with a light-transmitting film 81-1. In the example in FIG. 11, the transmittance is calculated by using the intensity of the light before transmission through the substrate 81 and the intensity of the light after transmission through the substrate 81. In the example in FIG. 11, the transmittance having a wavelength of 525 [nm] indicates the maximum value in the wavelength region at or below 700 [nm], being the lower limit of the biological window. Or, in the example in FIG. 11, the maximum value of transmittance of the light transmitted through the light-transmitting film 81-1 in the wavelength region at or below 700 [nm], being the biological window, for example, enters a range of within ±10% of the maximum value of the intensity of the wavelength of light emitted by the detecting light-emitting part 14-1 in FIG. 2. Thus, the light-transmitting film 81-1 is preferably one that selectively transmits the light emitted by the detecting light-emitting part 14-1 (e.g., the first light R1 in FIG. 10 (in the narrow sense, the reflected light R1' of the first light R1)). By the presence of the light-transmitting film 81-1, the flatness of the substrate 81 is improved, and a lowering of efficiency of the detecting light-emitting part 14-1 or the detecting light-receiving part 16-1 can be prevented to a certain extent. As illustrated in the example in FIG. 11, for example, in the case when the transmittance of the light having a wavelength of 525 [nm] indicates the maximum value (in the broad sense, peak value) in the visible light region, for example, the light-transmitting film 81-1 expresses green light.

Figure 12:
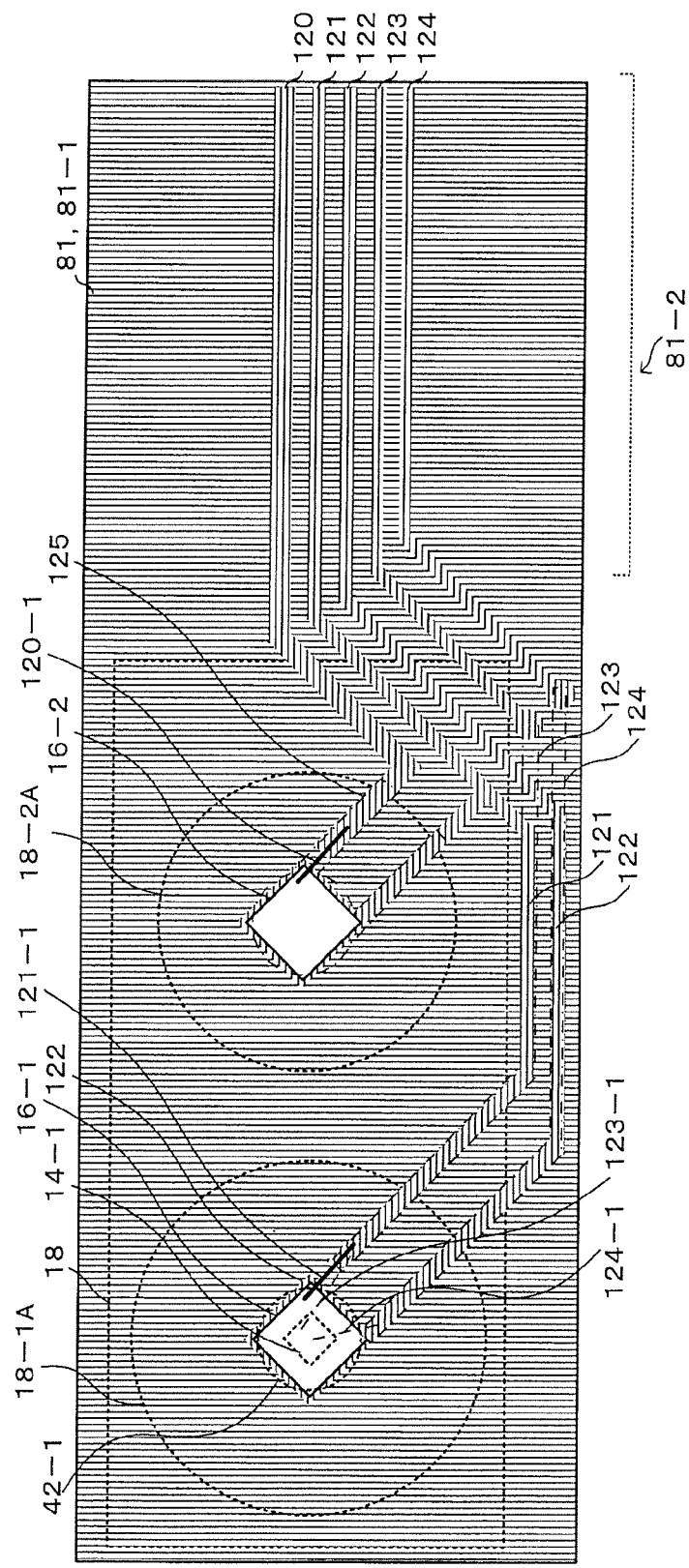
FIG. 12 is an example of the external appearance of the light-transmitting film.

FIG. 12 illustrates an example of the external appearance in plan view of the light-transmitting film 81-1 in FIG. 10. As illustrated in FIG. 12, the substrate 81 on which the light-transmitting film 81-1 is formed expresses a rectangular shape in plan view (e.g., on the side of the second detecting light-receiving part 16-1 in FIG. 10). In the example in FIG. 12, the detecting light-receiving part 16-1 and the correcting light-receiving part 16-2 are placed on the first surface (e.g., top surface) of the substrate 81. The light-transmitting film 81-1 may be formed in a region of the first surface of the substrate 81 where the detecting light-receiving part 16-1 and the correcting light-receiving part 16-2 are not placed.

Specifically, for example, a wiring 121 for connecting with the anode of the detecting light-receiving part 16-1, and for example, a wiring 122 for connecting with the cathode of the detecting light-receiving part 16-1, are formed on the first surface of the substrate 81. In the example in FIG. 12, for example, the wiring 121 is connected with the anode of the detecting light-receiving part 16-1 by way of a bonding wire 121-1, and the wiring 122 is directly connected with the cathode of the detecting light-receiving part 16-1. After the wiring 121 and the wiring 122 are formed on the substrate 81, the light-transmitting film 81-1 can be applied onto the first surface of the substrate 81. That is, the light-transmitting film 81-1 may be formed on top of the wiring 121 and on the wiring 122. However, the light-transmitting film may be applied selectively only in the region of the substrate 81 where the detecting light-receiving part 16-1 as well as the wiring 121 and the wiring 122 are not placed.

For example, a wiring 120 for connecting with the anode of the correcting light-receiving part 16-2, and for example, a wiring 121 for connecting with the cathode of the correcting light-receiving part 16-2, are formed on the first surface of the substrate 81. For example, the wiring 120 is connected with the anode of the correcting light-receiving part 16-2 by way of a bonding wire 120-1, and the wiring 121 is directly connected with the cathode of the correcting light-receiving part 16-2. The cathode of the correcting light-receiving part 16-2 is connected with the anode of the detecting light-receiving part 16-1 by way of the wiring 121.

The composite reflector 18 can then be formed or fixed on the substrate 81 (and the light-transmitting film 81-1). As illustrated in FIG. 12, the external shape of the composite reflector 18 describes a quadrangular shape. The external shape of a boundary 18-1A between the reflecting surface (domed surface) of the second detecting reflector 18-1 of the composite reflector 18 and the substrate 81 (light-transmitting film 81-1) describes a circular shape. A boundary 18-2A between the reflecting surface (domed surface) of the correcting reflector 18-2 of the composite reflector 18 and the substrate 81 (light-transmitting film 81-1) also expresses a circular shape. The light-transmitting film 81-1 may be applied selectively only in the light-transmitting regions inside the boundary 18-1A (circular shape) and the boundary 18-2A (circular shape). In other words, the light-transmitting film 81-1 may be applied selectively only in the light-transmitting regions where the light received by the detecting light-receiving part 16-1 and the light received by the correcting light-receiving part 16-2 are transmitted.

In the example in FIG. 12, the detecting light-emitting part 14-1 and the first detecting reflector 42-1 are placed on the second surface (e.g., bottom surface) of the substrate 81. Just as with the first surface, the light-transmitting film 81-1 may be formed in the region of the second surface of the substrate 81 where the detecting light-emitting part 14-1 and the first detecting reflector 42-1 are not placed. The light-transmitting film 81-1 is preferably formed at least in the light-transmitting region (the light-transmitting region in which light emitted by the detecting light-emitting part 14-1 and the external light are transmitted). In the example in FIG. 12, a wiring 123 is formed on the first surface on an end part 81-2 of the substrate 81, and is formed on the second surface, passing through the substrate 81. A second wiring 124 also is formed on the first surface on the end part 81-2 of the substrate 81, and is formed on the second surface, passing through the substrate 81. For example, the wiring 123 is connected with the cathode of the detecting light-emitting part 14-1 on the second surface side by way of a bonding wire 123-1, and a wiring 124 is connected with the cathode of the detecting light-emitting part 14-1 on the second surface side by way of a bonding wire 124-1. The wiring to the detecting light-emitting part 14-1, the detecting light-receiving part 16-1, and the correcting light-receiving part 16-2 can be easily brought to the outside, by arranging the end part 81-2 of the substrate 81 held between the composite reflector 18 and the protector 89 to protrude to the outside.

In the example in FIG. 12, a pseudo-wiring 125 is formed on the second surface (e.g., bottom surface) of the substrate 81. By the presence of the pseudo-wiring 125, a part of the transmitted light R3' (external light) transmitted through the test subject is suppressed from reaching the correcting reflector 18-2. The difference between the amount of transmitted light R3' (external light) received by the correcting light-receiving part 16-2 and the amount of transmitted light R3' (external light) received by the detecting light-receiving part 16-1 can thus be reduced.

Figure 13:
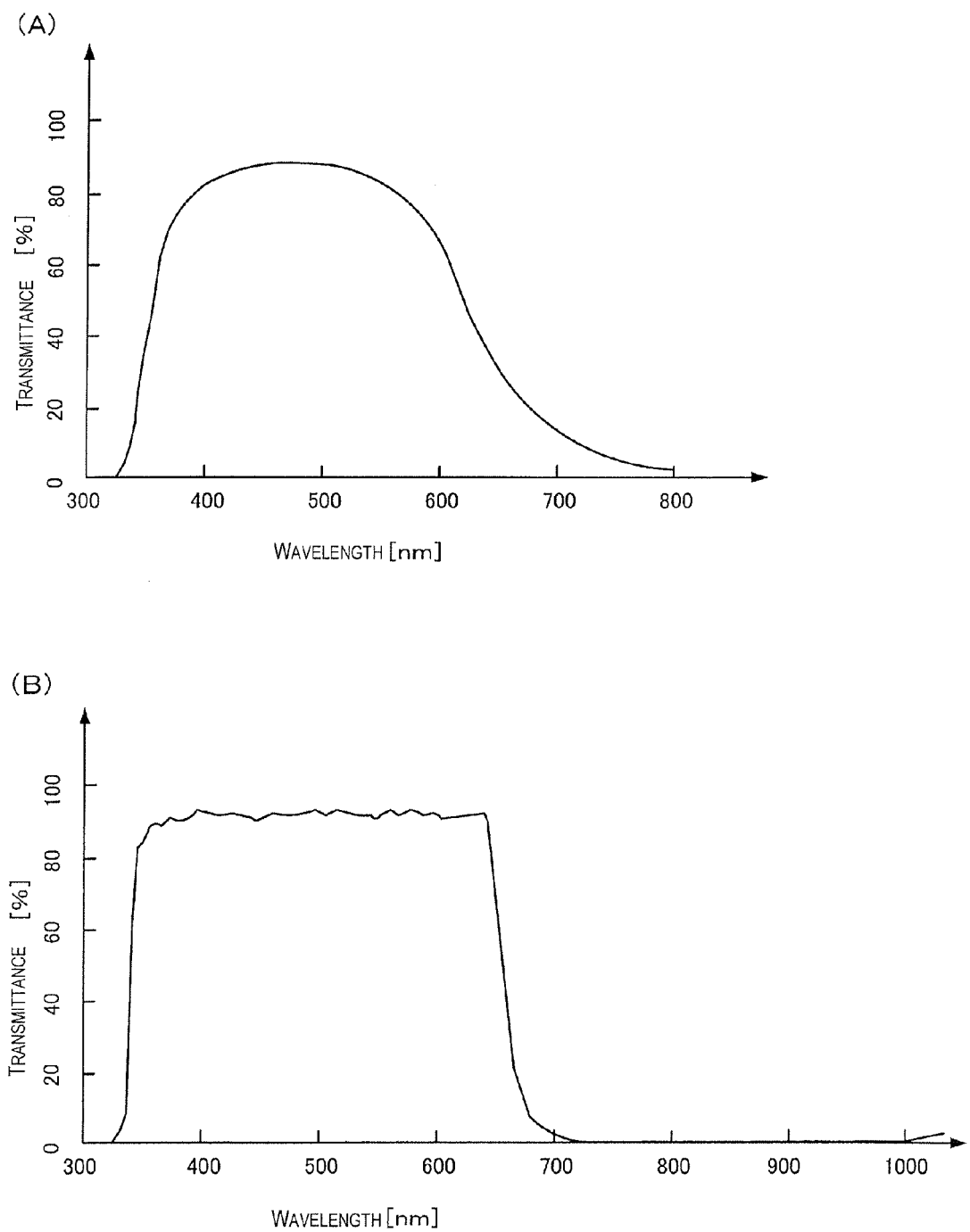
FIGS. 13(A) and (B) are graphs for describing the infrared-cutting filter.

FIGS. 13(A) and (B) illustrate graphs for describing the infrared-cutting filter 89-1 in FIG. 10. FIG. 13(A) illustrates one example of the transmission characteristics of light passing through the protector 89 without the infrared-cutting filter 89-1. FIG. 13(B) illustrates one example of the transmission characteristics of light passing through an infrared-absorbing material constituting the infrared-cutting filter 89-1. Referring to FIGS. 13(A) and (B), light (e.g., external light) in a range from 700 [nm] to 1100 [nm], referred to as the "biological window," can be prevented from entering by the presence of the infrared-cutting filter 89-1. The infrared-cutting filter 89-1 may be used for preventing the entrance of only a part of the wavelength (e.g., 700 [nm] to 800 [nm]) in the range from 700 [nm] to 1100 [nm].

Figure 14:
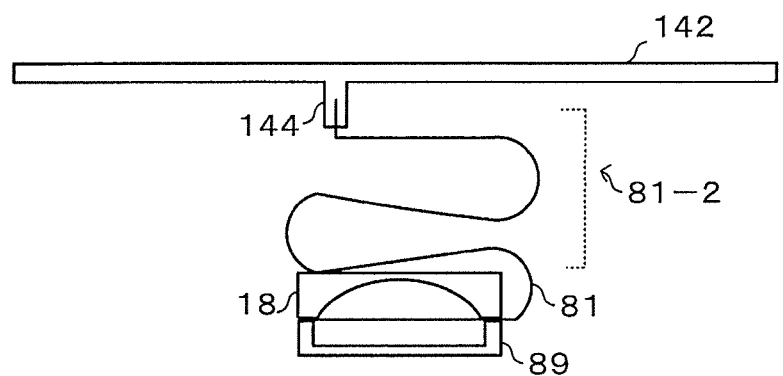
FIG. 14 is an example of storage of the board.

FIG. 14 illustrates an example of the substrate 81 being accommodated. In the example in FIG. 14, the substrate 81 may be made of a flexible board. Accordingly, the end part 81-2 of the substrate 81 is bendable. As illustrated in FIG. 14, the substrate 81 can be connected to a motherboard (e.g., a main board constituting a biological information measurement device, described further below) 142 of a computer in a state having bent the end part 81-2 of the substrate 81. In other words, a small-sized biological information detector can be provided by bending the substrate 81. In FIG. 14, the light-transmitting film 81-1 is omitted. The detecting light-emitting part 14-1, the detecting light-receiving part 16-1, and the correcting light-receiving part 16-2 also are omitted. The wiring to the detecting light-emitting part 14-1, the wiring to the detecting light-receiving part 16-1, and the wiring to the correcting light-receiving part 16-2 can be formed on the substrate 81, for example, as illustrated in FIG. 12, and the wiring can be connected between a control circuit of the motherboard 142 and the detecting light-emitting part 14-1, the detecting light-receiving part 16-1, and the correcting light-receiving part 16-2, by way of a connector 144.

The substrate 81 is held between the composite reflector 18 and the protector 89, whereby the composite reflector 18 is fixed to the substrate 81. The substrate 81 where the composite reflector 18 is fixed is locally unbendable, but the end part 81-2 of the substrate 81 where the composite reflector 18 is not fixed is bendable. Because the substrate 81 is held between the composite reflector 18 and the protector 89, the detecting light-emitting part 14-1, the detecting light-receiving part 16-1, and the correcting light-receiving part 16-2 can be mounted and supported on the substrate 81 even though the substrate 81 itself is a flexible board lacking rigidity.

Figure 15:
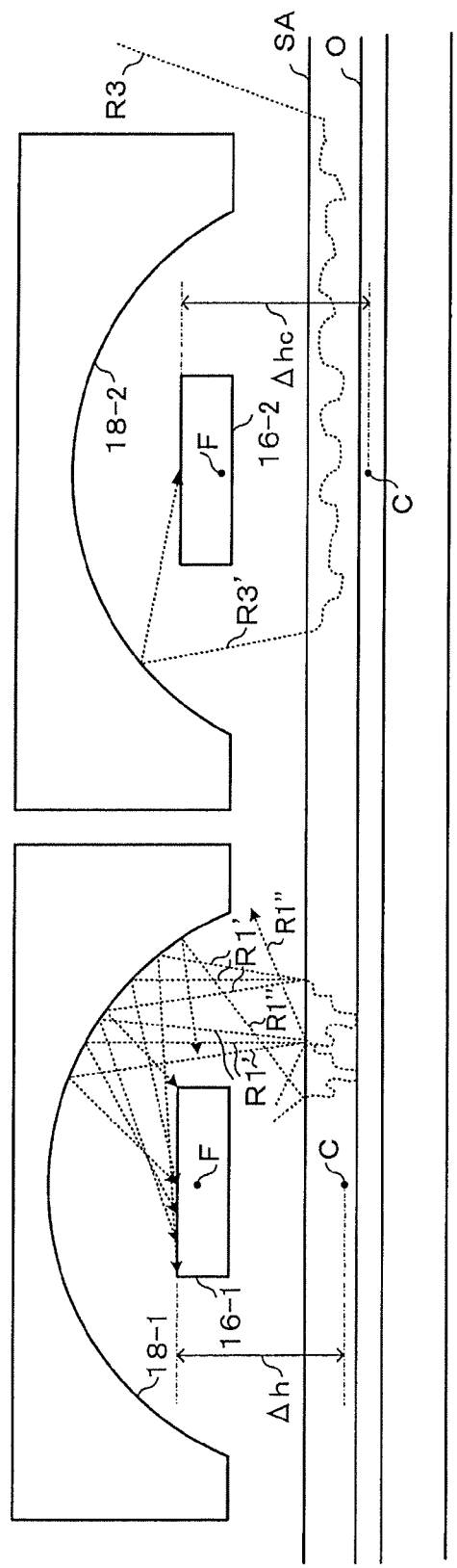
FIG. 15 is a diagram for describing the placement positions of the detecting reflector and the correcting reflector.

FIG. 15 is a diagram for describing the placement positions of the detecting reflector 18-1 and the correcting reflector 18-2 in FIG. 1, and the like. In FIG. 15, the detecting light-emitting part 14-1, and the like, in FIG. 1, and the like, are omitted. For example, the reflecting surface of the detecting reflector 18-1 (second detecting reflector 18-1) may be constituted as a spherical surface (in the broad sense, domed surface) so that the reflected light R1' of the first light R1 on the detection site O is reflected to the detecting light-receiving part 16-1. As illustrated in FIG. 15, the reflecting surface of the detecting reflector 18-1 (second detecting reflector 18-1) expresses an arc in sectional view. For example, the radius of the arc is 1000 [μm] to 15000 [μm]. The center C of the arc defining the spherical surface is disposed inside the test subject. In the case when there is a detection site O inside the test subject, the light R1" (directly reflected light) reflected by the outer surface SA of the test subject is invalid light not including the biological information. The present inventors recognized that, in the case when the reflecting surface of the detecting reflector 18-1 (second detecting reflector 18-1) is constituted as a spherical surface and the center C of the arc defining the spherical surface is set inside the test subject, the light (in the broad sense, noise) reflected by the outer surface SA of the test subject is suppressed by the detecting reflector 18-1 (second detecting reflector 18-1). In FIG. 15, the distance between the light-receiving surface of the detecting light-receiving part 16-1 and the center C of the arc defining the spherical surface is indicated as Δh.

The reflecting surface of the detecting reflector 18-1 (second detecting reflector 18-1) may be constituted as a parabolic surface (in the broad sense, domed surface) instead of a spherical surface. As illustrated in FIG. 15, the reflecting surface of the detecting reflector 18-1 (second detecting reflector 18-1) describes an arc in sectional view, but may describe a parabola instead of an arc. In FIG. 15, assuming that the reflecting surface of the detecting reflector 18-1 (second detecting reflector 18-1) is a parabolic surface, the focus of the parabola defining the parabolic surface is indicated by the reference numeral F. The focus F of the parabola defining the parabolic surface is disposed toward the side of the test subject, with reference to the light-receiving surface of the detecting light-receiving part 16-1. Because the light perpendicular to the outer surface SA of the test subject is reflected by the reflecting surface (parabolic surface) of the detecting reflector 18-1 (second detecting reflector 18-1), and is resolved on the focus F of the parabola defining the parabolic surface, the light (e.g., the reflected light R1' (valid light) of the first light R1) close to the light perpendicular to the outer surface SA of the test subject is more easily condensed by arranging the focus F so as not to coincide with the light-receiving surface of the detecting light-receiving part 16-1.

The reflecting surface of the correcting reflector 18-2 may be formed, for example, as a domed surface (spherical surface or parabolic surface), just as the detecting reflector 18-1 (second detecting reflector 18-1). As illustrated in FIG. 15, the reflecting surface of the correcting reflector 18-2 describes an arc in sectional view, but may describe a parabola. In the case when the reflecting surface of the correcting reflector 18-2 describes an arc in sectional view, the radius of the arc of the correcting reflector 18-2 may be set equal to the radius of the arc of the detecting reflector 18-1 (second detecting reflector 18-1), or may be set smaller than that radius. In FIG. 15, the distance between the light-receiving surface of the correcting reflector 16-2 and the center C of the arc defining the spherical surface of the correcting light-receiving part 16-2 is indicated by Δhc. By satisfying the relation Δhc>Δh, the difference between the amount of transmitted light R3' (external light) received by the correcting light-receiving part 16-2 and the amount of transmitted light R3' (external light) received by the detecting reflector 18-1 (second detecting reflector 18-1) can be reduced. In other words, by satisfying the relation Δhc>Δh, a relation S2 (area of the reflecting surface of the correcting reflector 18-2)<S1 (area of the reflecting surface of the detecting reflector 18-1 (second detecting reflector 18-1)) may also be satisfied. The relation S2<S1 may be satisfied by setting the radius of the arc of the correcting reflector 18-2 smaller than the radius of the arc of the detecting reflector 18-1 (second detecting reflector 18-1).

In FIG. 15, assuming that the reflecting surface of the correcting reflector 18-2 is a parabolic surface, the focus of the parabola defining the parabolic surface is indicated by the reference numeral F. The focus F of the parabola defining the parabolic surface is disposed toward the side of the test subject, with reference to the light-receiving surface of the correcting light-receiving part 16-2. In the case when the reflecting surface of the correcting reflector 18-2 describes a parabola in sectional view, the focal distance of the parabola of the correcting reflector 18-2 may be set equal to the focal distance of the parabola of the detecting reflector 18-1 (second detecting reflector 18-1), or may be set smaller than that focal distance. In FIG. 15, the distance between the light-receiving surface of the correcting reflector 16-2 and the focus F of the parabola defining the parabolic surface of the correcting light-receiving part 16-2 is indicated by Δhc.

For example, the detecting reflector 18-1 (second detecting reflector 18-1) is made of resin, and the top surface (the reflecting surface on the side of the detecting light-receiving part 16-1) is mirror-finished to have a reflective structure (in the narrow sense, a mirror-reflective structure). In other words, the detecting reflector 18-1 (second detecting reflector 18-1) may be rendered to mirror-reflect light and not to diffusely reflecting the light. In the case when the detecting reflector 18-1 (second detecting reflector 18-1) has a mirror-reflective structure, this detecting reflector 18-1 (second detecting reflector 18-1) can prevent reflection of the reflected light R1" (directly reflected light) of the first light R1, having a different angle of reflection from the angle of reflection of the reflected light R1' of the first light R1, to the detecting light-receiving part 16-1. In such a case, the detecting accuracy of the biological information detector is further improved. As illustrated in FIG. 15, because the origin of the reflected light R1' of the first light R1 is the detection site O inside the test subject, the angle of reflection of the reflected light R1' of the first light R1 is generally small. On the other hand, because the origin of the reflected light R1" of the first light R1 is the outer surface SA of the test subject, the angle of reflection of the reflected light R1" of the first light R1 is generally large. For example, the correcting reflector 18-2 also may be made of resin, and the top surface (the reflecting surface on the side of the correcting light-receiving part 16-2) may be mirror-finished to have a reflective structure (in the narrow sense, a mirror-reflective structure).

Figure 16:
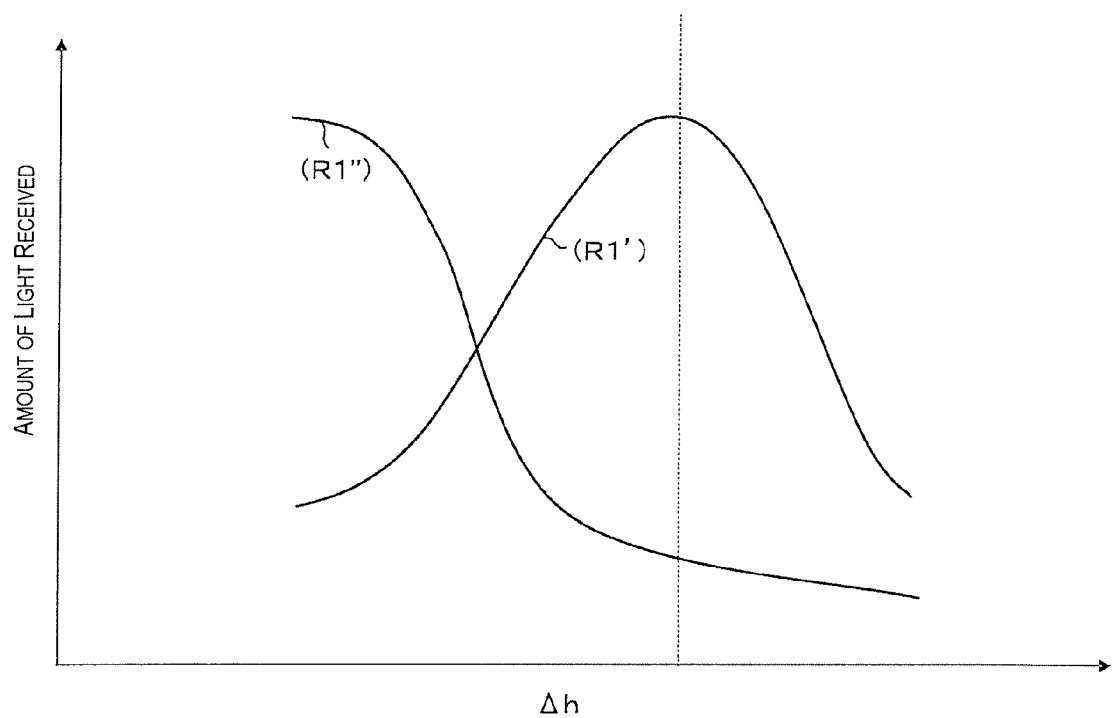
FIG. 16 is a graph of the relationship between the placement position of the detecting reflector and the amount of light received by the detecting light-receiving part.

FIG. 16 is a graph of the relationship between the placement position of the detecting reflector 18-1 in FIG. 15 and the amount of light received by the detecting light-receiving part 16-1. As illustrated in FIG. 16, as the distance Δh between the light-receiving surface of the detecting light-receiving part 16-1 and the center C of the arc defining the spherical surface becomes greater, the light (in the broad sense, noise, for example, corresponding to the reflected light R1") directly reflected by the outer surface SA of the test subject decreases, and the light (in the broad sense, biological information, for example, corresponding to the reflected light R1') increases and then decreases. The position of Δh can therefore be optimized. In the case when the reflecting surface of the detecting reflector 18-1 (second detecting reflector 18-1) is a parabolic surface, the distance between the light-receiving surface of the detecting light-receiving part 16-1 and the focus F of the parabola defining the parabolic surface also can be optimized.

2. Biological Information Measurement Device

Figure 17:
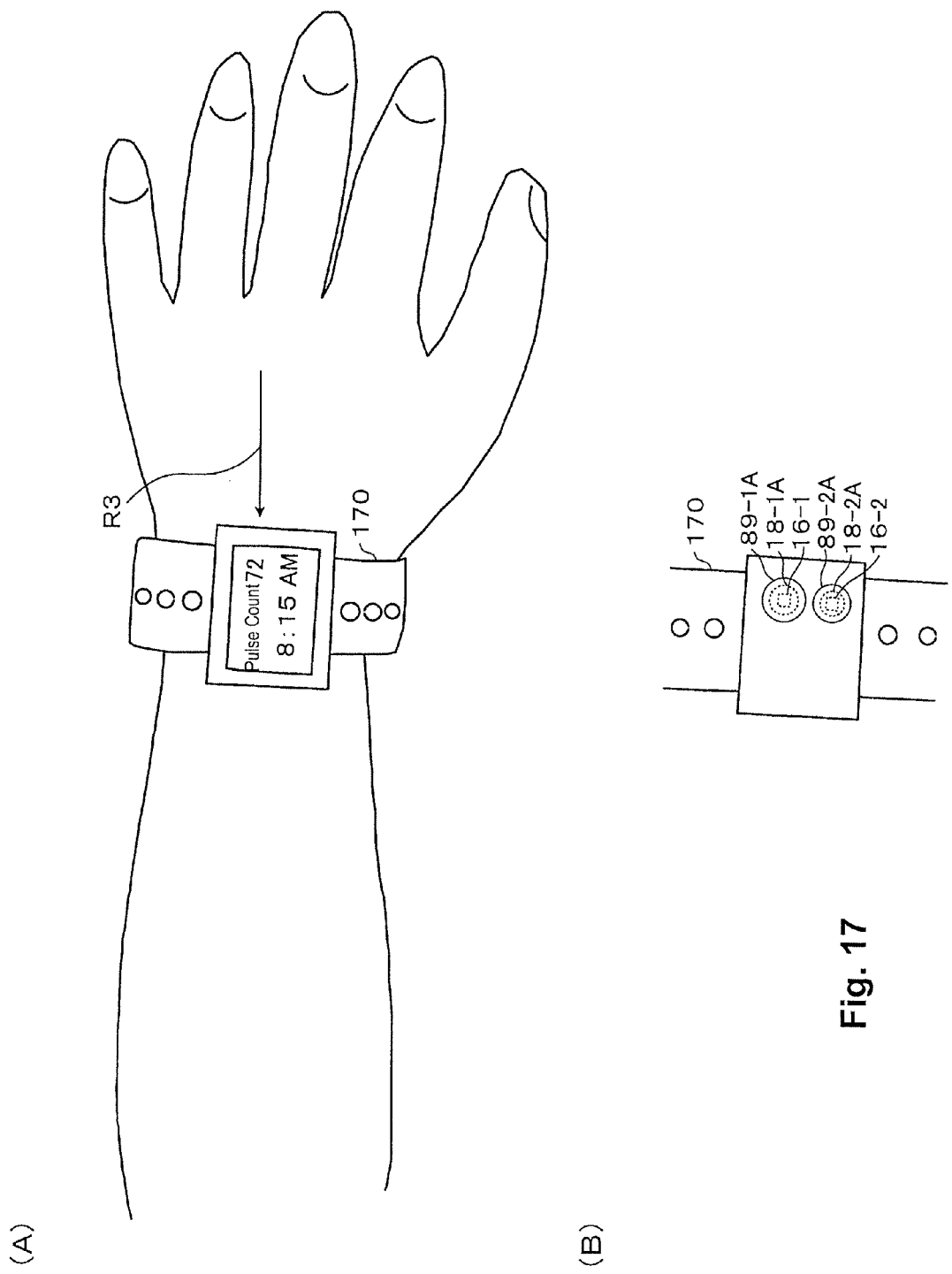
FIGS. 17(A) and (B) are examples of the external appearance of a biological information measurement device including a biological information detector.

FIGS. 17(A) and (B) are examples of the external appearance of a biological information measurement device including the biological information detector in FIG. 1, and the like. As illustrated in FIG. 17(A), for example, the biological information detector in FIG. 1 may further include a wristband 170 attachable to an arm (in the narrow sense, wrist) of the test subject (user) of the biological information detector. In the example in FIG. 17(A), the biological information is a pulse count, for example, as indicated by "72." The biological information detector is incorporated in a wristwatch, and the time (e.g., 8:15 a.m.) is displayed. As illustrated in FIG. 17(B), two openings are provided on the back cover of the wristwatch, and for example, the detection protector 89-1 in FIG. 10 is exposed in one of the two openings. For example, the correction protector 89-2A is exposed in the other of the two openings. One opening may be provided on the back cover of the wristwatch, and for example, the single protector 89 (composite protector) in FIG. 18 may be exposed in that opening. In the example in FIG. 17(B), the second detecting reflector 18-1 (detecting reflector 18-1) and the detecting light-receiving part 16-1 are incorporated in the wristwatch, and the boundary 18-1A between the reflecting surface (domed surface) of the second detecting reflector 18-1 and the substrate 81 is depicted by a dotted line. The correcting reflector 18-2 and the correcting light-receiving part 16-2 also are incorporated in the wristwatch, and the boundary 18-2A between the reflecting surface (domed surface) of the correcting reflector 18-2 and the substrate 81 is depicted by a dotted line. In the example in FIG. 17(B), the first detecting reflector 42-1, the detecting light-emitting part 14-1, and the like, are omitted.

In the example in FIG. 17(B), the detecting light-receiving part 16-1 (in the broad sense, first sensor unit) and the correcting light-receiving part (in the broad sense, correcting sensor unit) are disposed along the direction of extension of the wristband 170. The external light R3 enters between the wristband 170 and the arm from the surface side of the arm (the side of the wrist on the side where the biological information detector is worn). As illustrated in FIG. 17(A), the external light R3 enters, for example, from the direction from the peripheral side (e.g., the side of the back of the hand) toward the central side (shoulder joint) in plan view. The transmitted light R3' transmitted through the test subject proceeds toward the detecting light-receiving part 16-1 and the correcting light-receiving part 16-2. Accordingly, the detecting light-receiving part 16-1 and the correcting light-receiving part 16-2 may be disposed along the direction of extension of the wristband 170, so that the transmitted light R3' (external light R3) equally enters both the correcting sensor unit and the first sensor unit.

FIGS. 18(A) and (B) are diagrams for illustrating a composite light-receiving device. As illustrated in FIG. 1, and the like, the biological information detector has a detecting light-receiving part 16-1 and a correcting light-receiving part 16-2. As illustrated in FIG. 18(A), the anode of the detecting light-receiving part 16-1 is connected with the cathode of the correcting light-receiving part 16-2, and a composite light-receiving part 16 is formed. However, the anode of the detecting light-receiving part 16-1 may be made independent of the cathode of the correcting light-receiving part 16-2, and the signal (detecting light reception signal) generated in the detecting light-receiving part 16-1 may be extracted independently from the signal (correcting light reception signal) generated in the correcting light-receiving part 16-2.

In the example in FIG. 18(A), the composite light-receiving part 16 outputs a light reception signal expressing a difference between the detecting light reception signal and the correcting light reception signal. Because the detecting light reception signal generated in the detecting light-receiving part 16-1 contains biological information originating in the light emitted from the detecting light-emitting part 14-1 and noise information originating in the external light, and the correcting light reception signal generated in the correcting light-receiving part 16-2 contains noise information originating in the external light, the light reception signal expressing the difference between the detecting light reception signal and the correcting light reception signal can express only the biological information originating in the light emitted by the detecting light-emitting part 14-1. In other words, the composite biological information (the biological information in the detection site O and the first noise information originating in the external light R3) can be corrected by the noise information (the second noise information originating in the external light R3) from the correcting light-receiving part 16-2.

Figure 18:
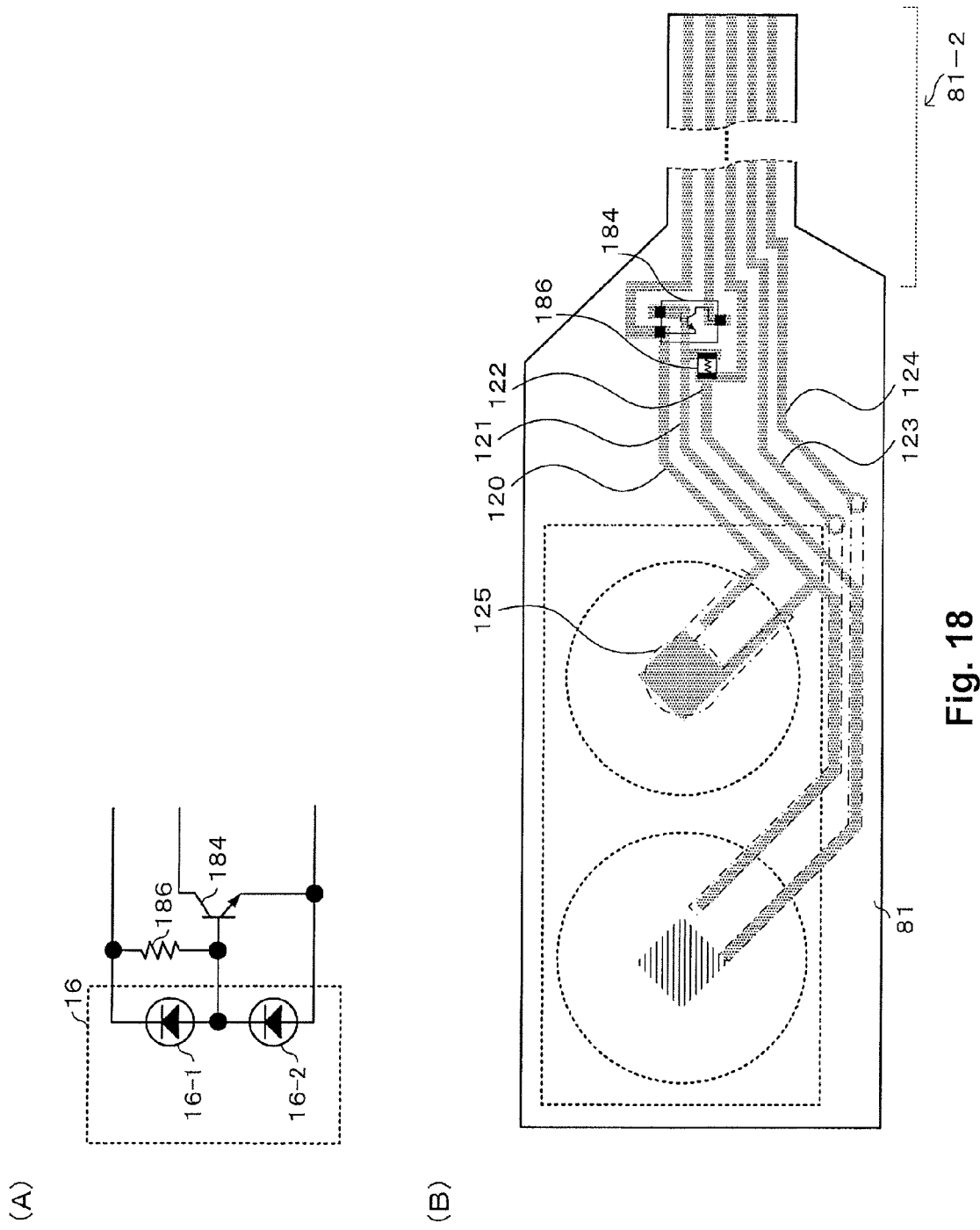
FIGS. 18(A) and (B) are diagrams for describing a composite light-receiving device.

As illustrated in the example in FIG. 18, a bipolar transistor (in the broad sense, amplifier 184) for inputting and amplifying on the basis of light reception signals of the composite light-receiving part 16 may be added. A resistor 186 may further be added between the anode of the detecting light-receiving part 16-1 and the cathode of the detecting light-receiving part 16-1. The amplifier 184 and the resistor 186 may be disposed, for example, as in FIG. 18(B). In FIG. 18(B), the shape of the end part 81-2 of the substrate 81 differs from the shape of the end part 81-2 in FIG. 12, and is narrowed down. As illustrated in FIG. 18(B), an unwanted part of the end part 81-2 can be removed.

Figure 19:
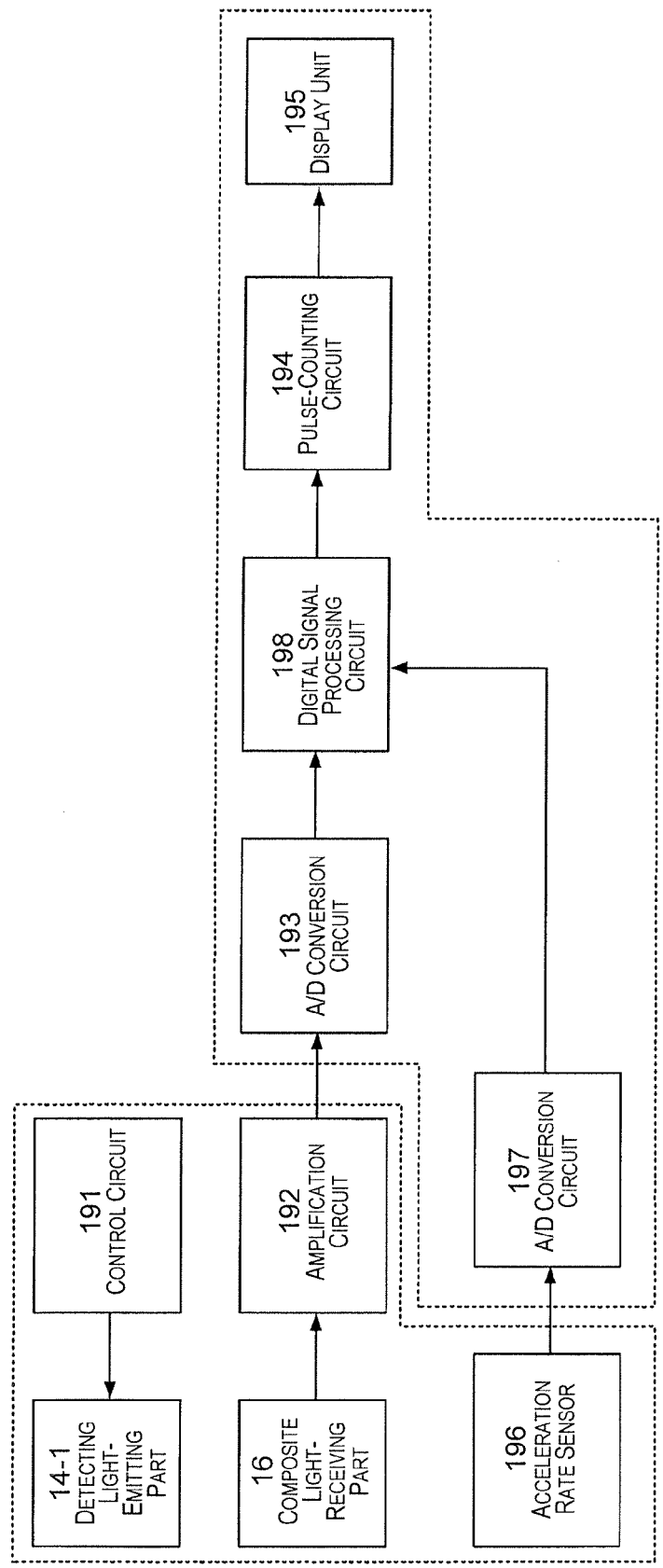
FIG. 19 is an example of the configuration of the biological information measurement device.

FIG. 19 illustrates an example of the configuration of the biological information measurement device. The biological information measurement device includes the biological information detector in FIG. 1, and the like, and a biological information measurement unit for measuring biological information from detecting light reception signals generated in the detecting light-receiving part 16-1 and correcting light reception signals generated in the correcting light-receiving part 16-2. As illustrated in FIG. 19, the biological information detector may have a detecting light-emitting part 14-1, a composite light-receiving part 16 (detecting light-receiving part 16-1 and correcting light-receiving part 16-2), and a control circuit 191 for the detecting light-emitting part 14-1. The biological information detector may further have an amplification circuit 192 for light-reception signals from the composite light-receiving part 16. The biological information measurement unit may have an A/D conversion circuit 193 for A/D-converting light-reception signals from the composite light-receiving part 16, and a pulse-counting circuit 194 for counting a pulse count. The biological information measurement unit may further have a display unit 195 for displaying the pulse count.

The biological information detector may have an acceleration rate sensor 196, and the biological information measurement unit may further have an A/D conversion circuit 197 for A/D-converting light-reception signals from the acceleration rate sensor 196, and a digital signal processing circuit 198 for processing the digital signals. The configuration example of the biological information measurement device is not limited to that shown in FIG. 19. The pulse-counting circuit 194 in FIG. 19 may be an MPU (micro-processing unit), being an electronic device incorporated in the biological information detector.

The control circuit 191 is used for driving the detecting light-emitting part 14-1. For example, the control circuit 191 is a constant-current circuit, and a given voltage (e.g., 6 [V]) is supplied to the detecting light-emitting part 14-1 by way of a protective resistor, and the current flowing to the detecting light-emitting part 14-1 is kept to a given value (e.g., 2 [mA]). The control circuit 191 can be used for driving the detecting light-emitting part 14-1 intermittently in order to reduce the consumption of current. The control circuit 191 is formed, for example, on the motherboard 142, and the wiring between the control circuit 191 and the detecting light-emitting part 14 is formed, for example, on the substrate 81 in FIG. 12.

The amplification circuit 192 in FIG. 19 can be used for removing a DC component from the light-reception signals (current) generated in the composite light-receiving part 16, extracting only an AC component, amplifying the AC component, and generating AC signals. In the amplification circuit 192, for example, the DC component at or below a given frequency is removed by a high-pass filter, and for example, the AC component is buffered by an op-amp. The light-reception signals include a pulse movement component and a body movement component. The amplification circuit 192 or the control circuit 191 can be used for supplying power current to the composite light-receiving part 16 in order to operate with reverse bias. In the case when the detecting light-emitting part 14 is driven intermittently, the power to the composite light-receiving part 16 also is supplied intermittently, and the AC component also is amplified intermittently. The amplification circuit 192 is formed, for example, on the motherboard 142, and the wiring between the amplification circuit 192 and the composite light-receiving part 16 is formed, for example, on the substrate 81 in FIG. 12. The amplification circuit 192 may also have an amplifier 184 for amplifying light-reception signals at the front end of the high-pass filter. In the case when the amplification circuit 192 has an amplifier 184, the amplifier 184 is formed, for example, on the substrate 81 in FIG. 18.

The A/D conversion circuit 193 in FIG. 19 is used for converting AC signals generated in the amplification circuit 192 to digital signals (first digital signals). The acceleration rate sensor 196 is used for detecting the weight acceleration rate, for example, on three axes (X, Y, and Z axes), and to generate acceleration rate signals. Movement of the body (arm), and accordingly movement of the biological information measurement device, is reflected in the acceleration rate signals. The A/D conversion circuit 197 in FIG. 19 is used for converting the acceleration rate signals generated in the acceleration rate sensor 196 to digital signals (second digital signals).

The digital signal processing circuit 198 in FIG. 19 is used for removing or reducing the body movement component in the first digital signals using the second digital signals. For example, the digital signal processing circuit 198 can be configured with a FIR filter or other adaptive filter. In the digital signal processing circuit 198, the first digital signals and the second digital signals are input to the adaptive filter, and filter output signals having removed or reduced noise are generated.

The pulse-counting circuit 194 in FIG. 19 is used for performing a frequency analysis of the filter output signals, for example, by fast Fourier transform (in the broad sense, discrete Fourier transform). The pulse-counting circuit 194 is used for identifying a frequency expressing the pulse component based on the result of the frequency analysis, and for counting the pulse count.

Although a detailed description was made concerning the present embodiment as stated above, persons skilled in the art should be able to easily understand that various modifications are possible without substantially departing from the scope and effects of the present invention. Accordingly, all of such examples of modifications are to be included in the scope of the present invention. For example, terms stated at least once together with different terms having broader sense or identical sense in the specification or drawings may be replaced with those different terms in any and all locations of the specification or drawings.

The entire disclosure of Japanese Patent Application No. 2010-000451, filed Jan. 5, 2010 is expressly incorporated by reference herein.

What is claimed is:

1. A biological information detector comprising:
   a first sensor unit subjected to detect composite information including biological information of a detection site of a test subject and first noise information originating in external light; and
   a second sensor unit subjected to detect second noise information originating in the external light;
   the first sensor unit having
      a light-emitting part subjected to emit a first light toward the detection site,
      a first light-receiving part subjected to receive the light including the biological information obtained from the first light emitted toward the detection site being reflected by the detection site, and the light including the first noise information obtained from the external light being transmitted through the test subject, and
      a first reflecting part subjected to reflect the light including the biological information and the light including the first noise information and leading the light to the first light-receiving part;
   the second sensor unit having
      a second light-receiving part subjected to receive the light including the second noise information obtained from the external light being transmitted through the test subject, and
      a second reflecting part subjected to reflect the light including the second noise information and leading the light to the second light-receiving part,
   the light-emitting part further emitting a second light toward a different direction from the detection site;
   the first sensor unit further having a third reflector for reflecting the second light and for leading the light to the detection site; and
   the first light-receiving part receiving the light including the biological information obtained from the second light being reflected by the detection site.

2. The biological information detector according to claim 1, wherein
   a relation S2<S1 is satisfied, where S1 is an area of a reflecting surface of the first reflecting part, and S2 is an area of a reflecting surface of the second reflecting part.

3. The biological information detector according to claim 1, wherein
   the first reflecting part is formed as a spherical surface or a parabolic surface;
   the second reflecting part is formed as a spherical surface or a parabolic surface; and
   a relation $\Delta hc > \Delta h$ is satisfied, where $\Delta h$ is a distance between a light-receiving surface of the first light-receiving part and a center of an arc defining the spherical surface of the first reflecting part or a focus of a parabola defining the parabolic surface of the first reflecting part, and $\Delta hc$ is a distance between a light-receiving surface of the second light-receiving part and a center of an arc defining the spherical surface of the second reflecting part or a focus of a parabola defining the parabolic surface of the second reflecting part.

4. A biological information measurement device comprising:
   the biological information detector described according to claim 3; and
   a biological information measurement unit for measuring the biological information on the basis of signals generated in the first light-receiving part and signals generated in the second light-receiving part.

5. The biological information measurement device according to claim 4, wherein
   the biological information is a pulse count.

6. A biological information detector comprising:
   a first sensor unit subjected to detect composite information including biological information of a detection site of a test subject and first noise information originating in external light; and
   a second sensor unit subjected to detect second noise information originating in the external light;
   the first sensor unit having
      a light-emitting part subjected to emit a first light toward the detection site,
      a first light-receiving part subjected to receive the light including the biological information obtained from the first light emitted toward the detection site being reflected by the detection site, and the light including the first noise information obtained from the external light being transmitted through the test subject, and
      a first reflecting part subjected to reflect the light including the biological information and the light including the first noise information and leading the light to the first light-receiving part;
   the second sensor unit having
      a second light-receiving part subjected to receive the light including the second noise information obtained from the external light being transmitted through the test subject, and
      a second reflecting part subjected to reflect the light including the second noise information and leading the light to the second light-receiving part,
   the second sensor unit further having a fourth reflector for reflecting a part of the light including the second noise information and for suppressing the light including the second noise information from reaching the second light-receiving part.

7. The biological information detector according to claim 6, wherein
   a relation S2<S1 is satisfied, where S1 is an area of a reflecting surface of the first reflecting part, and S2 is an area of a reflecting surface of the second reflecting part.

8. The biological information detector according to claim 6, wherein
   the first reflecting part is formed as a spherical surface or a parabolic surface;
   the second reflecting part is formed as a spherical surface or a parabolic surface; and
   a relation Δhc>Δh is satisfied, where Δh is a distance between a light-receiving surface of the first light-receiving part and a center of an arc defining the spherical surface of the first reflecting part or a focus of a parabola defining the parabolic surface of the first reflecting part, and Δhc is a distance between a light-receiving surface of the second light-receiving part and a center of an arc defining the spherical surface of the second reflecting part or a focus of a parabola defining the parabolic surface of the second reflecting part.

9. A biological information measurement device comprising:
   the biological information detector described according to claim 6; and
   a biological information measurement unit for measuring the biological information on the basis of signals generated in the first light-receiving part and signals generated in the second light-receiving part.

10. The biological information measurement device according to claim 9, wherein
    the biological information is a pulse count.

11. A biological information detector comprising:
    a first sensor unit subjected to detect composite information including biological information of a detection site of a test subject and first noise information originating in external light; and
    a second sensor unit subjected to detect second noise information originating in the external light;
    the first sensor unit having
       a light-emitting part subjected to emit a first light toward the detection site,
       a first light-receiving part subjected to receive the light including the biological information obtained from the first light emitted toward the detection site being reflected by the detection site, and the light including the first noise information obtained from the external light being transmitted through the test subject, and
       a first reflecting part subjected to reflect the light including the biological information and the light including the first noise information and leading the light to the first light-receiving part;
    the second sensor unit having
       a second light-receiving part subjected to receive the light including the second noise information obtained from the external light being transmitted through the test subject, and
    a second reflecting part subjected to reflect the light including the second noise information and leading the light to the second light-receiving part,
    the first sensor unit further having
       a wiring to the light-emitting part, and
       a wiring to the first light-receiving part, and
    the second sensor unit further having
       a wiring to the second light-receiving part, and
       a pseudo-wiring for suppressing the light including the second noise information from reaching the second light-receiving part.

12. The biological information detector according to claim 11, wherein
    a relation S2<S1 is satisfied, where S1 is an area of a reflecting surface of the first reflecting part, and S2 is an area of a reflecting surface of the second reflecting part.

13. The biological information detector according to claim 11, wherein
    the first reflecting part is formed as a spherical surface or a parabolic surface;
    the second reflecting part is formed as a spherical surface or a parabolic surface; and
    a relation Δhc>Δh is satisfied, where Δh is a distance between a light-receiving surface of the first light-receiving part and a center of an arc defining the spherical surface of the first reflecting part or a focus of a parabola defining the parabolic surface of the first reflecting part, and Δhc is a distance between a light-receiving surface of the second light-receiving part and a center of an arc defining the spherical surface of the second reflecting part or a focus of a parabola defining the parabolic surface of the second reflecting part.

14. A biological information measurement device comprising:
the biological information detector described according to claim 11; and
a biological information measurement unit for measuring the biological information on the basis of signals generated in the first light-receiving part and signals generated in the second light-receiving part.

15. The biological information measurement device according to claim 14, wherein
the biological information is a pulse count.

* * * * *